United States Patent
Nagrath et al.

(10) Patent No.: US 10,073,024 B2
(45) Date of Patent: Sep. 11, 2018

(54) MICROFLUIDIC DEVICE AND METHOD FOR DETECTING RARE CELLS

(71) Applicant: The Regents Of The University Of Michigan, Ann Arbor, MI (US)

(72) Inventors: Sunitha Nagrath, Ann Arbor, MI (US); Hyeun Joong Yoon, Ann Arbor, MI (US); Eric Lin, Ann Arbor, MI (US); Max S. Wicha, Ann Arbor, MI (US); Lianette Rivera Baez, Ann Arbor, MI (US); Diane M. Simeone, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 135 days.

(21) Appl. No.: 14/439,429

(22) PCT Filed: Oct. 29, 2013

(86) PCT No.: PCT/US2013/067315
§ 371 (c)(1),
(2) Date: Apr. 29, 2015

(87) PCT Pub. No.: WO2014/070776
PCT Pub. Date: May 8, 2014

(65) Prior Publication Data
US 2015/0293010 A1 Oct. 15, 2015

Related U.S. Application Data

(60) Provisional application No. 61/795,860, filed on Oct. 29, 2012.

(51) Int. Cl.
*G01N 15/10* (2006.01)
*B01L 3/00* (2006.01)
(Continued)

(52) U.S. Cl.
CPC .... *G01N 15/1056* (2013.01); *B01L 3/502715* (2013.01); *B01L 3/502753* (2013.01);
(Continued)

(58) Field of Classification Search
CPC ................ G01N 15/1056; G01N 15/10; B01L 3/502715; B01L 3/5021; B01L 3/502;
(Continued)

(56) References Cited

U.S. PATENT DOCUMENTS 5,376,252 A * 12/1994 Ekstrom ................ B01D 57/02
 204/603
5,770,528 A 6/1998 Mumick et al.
(Continued)

FOREIGN PATENT DOCUMENTS

EP 1 214 361 A 2/2001
EP 2 335 075 A 3/2010
(Continued)

OTHER PUBLICATIONS

Yu et al., "RNA sequencing of pancreatic circulating tumour cells implicates WNT signalling in metastasis", Nature, vol. 487, Jul. 26, 2012, pp. 510-514.
(Continued)

*Primary Examiner* — Christine T Mui
(74) *Attorney, Agent, or Firm* — Howard & Howard Attorneys PLLC

(57) ABSTRACT

A microfluidic device for detecting rare cells in a fluid sample comprises the rare cell and other cells. The microfluidic device comprises an inlet for receiving the fluid sample, a labyrinth channel structure in fluid communication with the inlet, and an outlet in fluid communication with the labyrinth channel structure for collecting the rare cells separated from the other cells in the fluid sample. The labyrinth channel structure comprises at least one channel
(Continued)

through which the fluid sample flows. The at least one channel has a plurality of segments and a plurality of corners with each corner defined between adjacent segments. The presence of the plurality of corners induces separation of the rare cells from the other cells in the fluid sample as the rare cells move to a first equilibrium position within the at least one channel when a ratio of inertial lift forces ($F_Z$) and Dean flow ($F_D$) of the fluid sample is from 2 to 10.

20 Claims, 15 Drawing Sheets

(51) Int. Cl.

| | | |
|---|---|---|
| *G01N 33/50* | (2006.01) | |
| *G01N 33/574* | (2006.01) | |
| *G01N 15/02* | (2006.01) | |
| *C12Q 1/04* | (2006.01) | |
| *G01N 15/00* | (2006.01) | |

(52) U.S. Cl.
CPC .... *B01L 3/502761* (2013.01); *G01N 15/0272* (2013.01); *G01N 33/5005* (2013.01); *G01N 33/574* (2013.01); *B01L 2200/0652* (2013.01); *B01L 2300/0816* (2013.01); *B01L 2300/0864* (2013.01); *B01L 2300/0883* (2013.01); *G01N 2015/008* (2013.01); *G01N 2015/0065* (2013.01); *G01N 2015/0288* (2013.01); *G01N 2015/1006* (2013.01); *G01N 2015/1081* (2013.01)

(58) Field of Classification Search
CPC ............... B01L 3/50; B01L 2300/0186; B01L 2300/0809; B01L 2300/08; C12Q 1/04; C12Q 1/02
USPC ...... 422/503, 502, 501, 500, 50; 435/34, 29, 435/308.1
See application file for complete search history.

(56) References Cited

U.S. PATENT DOCUMENTS

| | | | |
|---|---|---|---|
| 5,776,487 A | | 7/1998 | Maxfield Wilson et al. |
| 6,485,690 B1* | | 11/2002 | Pfost .................... B01J 19/0046 422/552 |
| 6,803,019 B1* | | 10/2004 | Bjornson ......... G01N 27/44791 422/504 |
| 7,179,867 B2 | | 2/2007 | Chang et al. |
| 7,332,288 B2 | | 2/2008 | Terstappen et al. |
| 7,846,393 B2 | | 12/2010 | Tai et al. |
| 8,548,219 B2 | | 10/2013 | Ortyn et al. |
| 9,140,697 B2 | | 9/2015 | Tseng et al. |
| 2004/0005582 A1* | | 1/2004 | Shipwash ......... G01N 33/54366 435/6.19 |
| 2005/0181463 A1 | | 8/2005 | Rao et al. |
| 2006/0160243 A1 | | 7/2006 | Tang et al. |
| 2007/0224591 A1 | | 9/2007 | Gui et al. |
| 2007/0263477 A1* | | 11/2007 | Sudarsan ............... B01F 5/0644 366/3 |
| 2008/0267845 A1* | | 10/2008 | Hoglund ............... B01F 5/0451 422/224 |
| 2009/0303472 A1 | | 12/2009 | Zhao et al. |
| 2010/0028681 A1 | | 2/2010 | Dai et al. |
| 2010/0068105 A1 | | 3/2010 | Green |
| 2010/0255479 A1 | | 10/2010 | Mikolajczyk et al. |
| 2010/0255581 A1 | | 10/2010 | Naqvi et al. |
| 2011/0091864 A1* | | 4/2011 | Karlsson ................. B03C 5/005 435/4 |
| 2011/0096327 A1* | | 4/2011 | Papautsky .......... B01D 21/0087 356/335 |
| 2011/0189650 A1 | | 8/2011 | Ayliffe et al. |
| 2012/0003711 A1 | | 1/2012 | Tseng et al. |
| 2012/0040843 A1 | | 2/2012 | Ducree et al. |
| 2012/0209116 A1 | | 8/2012 | Hossack et al. |
| 2012/0300576 A1 | | 11/2012 | Li et al. |
| 2013/0129829 A1 | | 5/2013 | He |
| 2013/0261266 A1 | | 10/2013 | Bunyard et al. |
| 2014/0186316 A1 | | 7/2014 | Tseng et al. |
| 2014/0315213 A1 | | 10/2014 | Nagrath et al. |
| 2015/0285808 A1 | | 10/2015 | Nagrath et al. |
| 2015/0293010 A1 | | 10/2015 | Nagrath et al. |

FOREIGN PATENT DOCUMENTS

| | | |
|---|---|---|
| WO | WO 01/09198 | 2/2001 |
| WO | WO 2009/051734 A1 | 4/2009 |
| WO | WO 2010/028160 A1 | 3/2010 |
| WO | WO 2010/108003 A2 | 9/2010 |
| WO | WO 2010/124227 A2 | 10/2010 |
| WO | WO 2011/049963 A2 | 4/2011 |
| WO | WO 2011/094279 A1 | 8/2011 |
| WO | WO 2012/094642 A2 | 7/2012 |
| WO | WO 2013/049636 A1 | 4/2013 |
| WO | WO 2013/116523 A1 | 8/2013 |
| WO | WO 2014/022581 A1 | 2/2014 |
| WO | WO 2014/036951 A1 | 3/2014 |
| WO | WO 2014/072465 A1 | 5/2014 |
| WO | WO 2014/120265 A1 | 8/2014 |

OTHER PUBLICATIONS

Zhang et al. "Binding Affinities/Avidities of Antibody-Antigen Interactions: Quantification and Scale-Up Implications", Biotechnology and Bioengineering, vol. 95, No. 5, Dec. 5, 2006, pp. 812-829.
Zhang et al. "Electrospun TiO2 Nanofiber-Based Cell Capture Assay for Detecting Circulating Tumor Cells from Colorectal and Gastric Cancer Patients", Advanced Materials 24, 2012, pp. 2756-2760.
Zhang et al. "Experimental observation of the quantum Hall effect and Berry's phase in graphene", Nature, vol. 438, Issue 7065, Nov. 2005, pp. 201-204.
Zheng et al. "A high-performance microsystem for isolating circulating tumor cells", Lab Chip, The Royal Society of Chemistry, 2011, pp. 3269-3276.
Zheng et al. "Membrane microfilter device for selective capture, electrolysis and genomic analysis of human circulating tumor cells", Journal of Chromatography A 1162, pp. 154-161 (2007).
"Circulating tumor cells: the Grand Challenge", Lab Chip, The Royal Society of Chemistry, 2011, pp. 375-377.
International Search Report for Application No. PCT/US2012/058013 dated Feb. 14, 2013, 4 pages.
Adams et al. "Highly efficient circulating tumor cell isolation from whole blood and label-free enumeration using polymer-based microfluidics with an integrated conductivity sensor", J. Am. Chemical Society, 130, 2007, pp. 8633-8641.
Allard et al. "Tumor Cells Circulate in the Peripheral Blood of All Major Carcinomas but not in Healthy Subjects or Patients With Nonmalignant Diseases", Clinical Cancer Research 10, 2004, pp. 6897-6904.
American Association of Cancer Research, "Annual Meeting-Capture and Release of Circulating Tumor Cells by Temperature-Sensitive Graphene Oxide-Polymer Composite", Apr. 19, 2015.
Andreopoulou et al. "Comparison of assay methods for detection of circulating tumor cells in metastatic breast cancer: AdnaGen AdnaTest Breast Cancer Select/Detect(TM) versus Veridex CellSearch(TM) system", Int. J. Cancer: 130, 2012, pp. 1590-1597.
Antolovic et al. "Heterogeneous detection of circulating tumor cells in patients with colorectal cancer by Immunomagnetic enrichment using different EpCAM-specific antibodies", BMC Biotechnology 10, 35, 2010, 8 pages.
Barreto et al. "Nanomaterials: Applications in Cancer Imaging and Therapy" Advanced Materials 23, 2011, pp. H18-H40.

(56) References Cited

OTHER PUBLICATIONS

Bednarz-Knoll et al. "Plasticity of disseminating cancer cells in patients with epithelial malignancies" Cancer and Metastasis Reviews, Jun. 26, 2012, 15 pages.
Chen et al., "Aptamer-Enabled Efficient Isolation of Cancer Cells from Whole Blood Using a Microfluidic Device", Anal. Chem., 1:84(9), May 1, 2012, pp. 4199-4206.
Cohen et al. "Relationship of Circulating Tumor Cells to Tumor Response, Progression-Free Survival, and Overall Survival in Patients With Metastatic Colorectal Cancer" Journal of Clinical Oncology 26, 2008, pp. 3213-3221.
Cristofanilli et al. "Circulating Tumor Cells, Disease Progression, and Survival in Metastatic Breast Cancer", New England Journal of Medicine 351, 2004, pp. 781-791.
De Bono et al. "Circulating Tumor Cells Predict Survival Benefit from Treatment in Metastatic Castration-Resistant Prostate Cancer", Clinical Cancer Research 14, 2008, pp. 6302-6309.
Dikin et al. "Preparation and characterization of graphene oxide paper", Nature 448, 2007, pp. 457-460.
Dobrovolskaia et al. "Immunological properties of engineered nanomaterials", Nat Nano 2, 2007, pp. 469-478.
Dreyer et al. "The chemistry of graphene oxide", Chemical Society Reviews 39, 2010, pp. 228-240.
Eda et al. "Large-area ultrathin films of reduced graphene oxide as a transparent and flexible electronic material", Nat, Nano 3, 2008, pp. 270-274.
Farace et al. "A direct comparison of CellSearch and ISET for circulating tumour-cell detection in patients with metastic carcinomas", British Journal of Cancer 105, 2011, pp. 847-853.
Fehm et al. "Detection and characterization of circulating tumor cells in blood of primary breast cancer patients by RT-PCR and comparison to status of bone marrow disseminated cells", Breast Cancer Research 11:R59, 2009, 9 pages.
Fehm et al. "HER2 status of circulating tumor cells in patients with metastatic breast cancer: a prospective, multicenter trial", Breast Cancer Res. Treat, 124, 2010, pp. 403-412.
Geim et al. "The rise of graphene", Nature Materials, vol. 6, 2007, pp. 183-191.
Gleghorn et al. "Capture of circulating tumor cells from whole blood of prostate cancer patients using geometrically enhanced differential immunocapture (GEDI) and a prostate-specific antibody", Lab on a Chip 10, 2010, pp. 27-29.
Hanahan et al., "Hallmarks of Cancer: The Next Generation", Cell, 144, Mar. 4, 2011, pp. 646-674.
Haugaard et al. "In vitro detection of CTCs with the CytoTrack method", a poster presentation retrieved from www.cytotrack.dk/page12 on Apr. 16, 2014, 1 page.
Hayes et al. "Circulating Tumor Cells at Each Follow-up Time Point during Therapy of Metastatic Breast Cancer Patients Predict Progression-Free and Overall Survival", Clin Cancer Res 12, 2006, pp. 4218-4224.
Hillig et al. "In vitro validation of an ultra-sensitive scanning fluorescence microscope for analysis of Circulating Tumor Cells", APMIS 2013 published by John Wiley & Sons Ltd, 7 pages.
Hillig et al. "Monitoring CTC in metastatic breast cancer patients using the CytoTrack method", a poster presentation retrieved from www.cytrotrack.dk/page12 on Apr. 16, 2014, 1 page.
Hummers et al. "Preparation of graphitic oxide", Journal of the American Chemical Society, vol. 80, Mar. 1958, p. 1339.
Amnis Corporation, "Brochure for ImageStreamX, Imaging Flow Cytometer", 2012, 16 pages.
Jung et al. "A graphene oxide based immuno-biosensor for pathogen detection", Angew. Chem. 122, 2010, pp. 5844-5847.
Kaiser "Cancer's Circulation Problem", Science 327, 2010, pp. 1072-1074.
Kim et al. "Nanomedicine", New England Journal of Medicine 363, 2010, pp. 2434-2443.
Kurkuri et al. "Plasma functionalized PDMS microfluidic chips: towards point-of-care capture of circulating tumor cells", Journal of Materials Chemistry 21, 2011, pp. 8841-8848.

Lee et al. "Nanowire Substrate-Based Laser Scanning Cytometry for Quantitation of Circulating Tumor Cells", Nano Letters 12, 2012, pp. 2697-2704.
Li et al. "Processable aqueous dispersions of graphene nanosheets", Nature Nanotechnology, vol. 3, 2008, pp. 101-105.
Li et al. "Highly conducting graphene sheets and Langmuir-Blodgett films", Nat. Nano. 3, 2008, pp. 538-542.
Lin et al. "Portable Filter-Based Microdevice for Detection and Characterization of Circulating Tumor Cells", Clinical Cancer Research 16, 2010, pp. 5011-5018.
Liu et al. "Biocompatable graphene oxide-based glucose biosensors", Langmuir 26(9), 2010, pp. 6158-6160.
Liu et al. "Supramolecular chemistry on water-soluble carbon nanotubes for drug loading and delivery", ACS Nanovol. 1, 2007, pp. 50-56.
Liu et al. "Intercalation of Organic Ammonium Ions into Layered Graphite Oxide", Langmuir 18, 2002, pp. 4926-4932.
Liu et al. "PEGylated nanographene oxide for delivery of water-insoluble cancer drugs", J Am Chem Soc 130, 2008, pp. 10876-10877.
Liu et al. "Preparation of carbon nanotube bioconjugates for biomedical applications", Nat. Protocols 4, 2009, pp. 1372-1381.
Loh et al. "Graphene oxide as a chemically tunable platform for optical applications", Nat Chem 2, 2010, pp. 1015-1024.
Lopez-Riquelme et al. "Imaging cytometry for counting circulating tumor cells: comparative analysis of the CellSearch vs. ImageStream systems", APMIS, 121, published by John Wiley & Sons Ltd., 2013, pp. 1139-1143.
Pantel et al., "Circulating Tumour Cells in Cancer Patients: Challenges and Perspectives", Trends. Mol. Med. 2010, 16(9), pp. 398-406.
Park et al. "Chemical methods for the production of graphenes" Nature Nanotechnology, vol. 4, Apr. 2009, pp. 217-224.
Pierce Biotechnology, Inc., "GMBS and Sulfo-GMBS" Rockford, IL, Jul. 2005, retrieved from http://www.piercenet.com/instructions/2161763.pdf on Apr. 16, 2014, 3 pages.
Poveda et al., "Circulating tumor cells predict progression free survival and overall survival in patients with relapsed/recurrent advanced ovarian cancer", Gynecologic Oncology, vol. 122, 2011, pp. 567-572.
Powell et al. "Single Cell Profiling of Circulating Tumor Cells: Transcriptional Heterogeneity and Diversity from Breast Cancer Cell Lines", PLoS one, vol. 7, Issue 5, May 2012, pp. 1-11.
Punnoose et al. "Evaluation of Circulating Tumor Cells and Circulating Tumor DNA in Non-Small Cell Lung Cancer: Association with Clinical Endpoints in a Phase 11 Clinical Trial of Pertuzumab and Erlotinib", Clinical Cancer Research, 2012, pp. 2391-2401.
Punnoose et al. "Molecular Biomarker Analyses Using Circulating Tumor Cells" PLoS ONE vol. 5, Issue 9, e12517, 2010, 12 pages.
Rahbari et al., "Compartmental differences of circulating tumor cells in colorectal cancer", Annals of Surgical Oncology, vol. 19, 2012, pp. 2195-2202.
Ramanathan et al. "Functionalized graphene sheets for polymer nanocomposites" Nat Nanotechnol 3, 2008 pp. 327-331.
Reddy et al., "Pulmonary venous blood sampling significantly increases the yield of circulating tumor cells in early-stage lung cancer", The Journal of Thoracic and Cardiovascular Surgery, 2015, pp. 852-858.
Riethdorf et al. "Detection of Circulating Tumor Cells in Peripheral Blood of Patients with Metastatic Breast Cancer: A Validation Study of the CellSearch System" Clin Cancer Res 13, 2007, pp. 920-928.
Roy et al. "New directions in thermoresponsive polymers", The Royal Society of Chemistry, 2013, pp. 7214-7243.
Rudin et al. "Phase II Study of Single-Agent Navitoclax (ABT-263) and Biomarker Correlates in Patients with Relapsed Small Cell Lung Cancer", Clinical Cancer Research, Jun. 1, 2012, pp. 3163-3169.
Sarioglu et al., "A microfluidic device for label-free, physical capture of circulating tumor cell clusters", Nature Methods, vol. 12, No. 7, 2015, pp. 685-691.
Schmittgen et al., "Analyzing real-time PCR data by the comparative C(T) method", Nature Protocols, vol. 3, No. 6, 2008, pp. 1101-1108.

(56) References Cited

OTHER PUBLICATIONS

Sequist et al., "An Exciting New Tool to Detect Circulating Tumor Cells in Lung Cancer Patients", Journal of Thoracic Oncology, vol. 4, No. 3, Mar. 2009, pp. 281-283.
Shah et al., "Biopolymer System for Cell Recovery from Microfluidic Cell Capture Devices" American Chemical Society Publications, 2012, pp. 3682-3688.
Shao et al. "Graphene based electrochemical sensors and biosensors: A review", Electroanalysis 22, No. 10, 2010, pp. 1027-1036.
Shanker et al., "Microfluidic Device with Polyer-Graphene Oxide Composite Platform for Efficient Capture and Release of Circulating Tumor Cells," University of Michigan, Date: 2015, 1 page.
Sheng et al. "Aptamer-Enabled Efficient Isolation of Cancer Cells from Whole Blood Using a Microfluidic Device" Analytical Chemistry 84, 2012, pp. 4199-4206.
Sienel et al., "Tumour cells in the tumour draining vein of patients with non-small cell lung cancer: detection rate and clinical significance", European Journal of Cardio-Thoracic Surgery: Official Journal of the European Association for Cardio-thoracic Surgery, vol. 23, 2003, pp. 451-456.
Smirnov et al., "Global Gene Expression Profiling of Circulating Tumor Cells", American Association for Cancer Research, Jun. 15, 2005, pp. 4993-4997.
Stankovich et al. "Graphene-based composite materials" Nature 442, 2006, pp. 282-286.
Stankovich et al. "Synthesis and exfoliation of isocyanate-treated graphene oxide nanoplatelets" Carbon, vol. 44, 2006, pp. 3342-3347.
Stott et al., "Isolation and characterization of circulating tumor cells from patients with localized and metastatic prostate cancer", Science Translational Medicine, vol. 2, Issue 25, 2010, pp. 1-10.
Sun et al. "Circulating tumor cells: advances in detection methods, biological issues, and clinical relevance" J Cancer Research Clinical Oncology, 2011, pp. 1151-1173.
Sun et al. "Nano-Graphene Oxide for Cellular Imaging and Drug Delivery" Nano Res 1, 2008, pp. 203-212.
Suzuki et al., "Aberrant methylation of SPARC in human lung cancers", British Journal of Cancer, vol. 92, 2005, pp. 942-948.
Ting et al., "Single-cell RNA sequencing identifies extracellular matrix gene expression by pancreatic circulating tumor cells", Cell Reports, vol. 8, 2014, pp. 1905-1918.
Tjensvoll et al. "Circulating tumor cells in pancreatic cancer patients: Methods of detection and clinical implications" Int. J. Cancer: 134, 2014, pp. 1-8.
Tymosiak-Zielinska et al. "Interfacial properties of polycrystalline gold electrodes in tetraalkylammonium electrolytes" Electrochimica Acta 46, 2001, pp. 3073-3082.
Wang et al. "Chemical self-assembly of graphene sheets" Nano Research, vol. 2, Feb. 2009, pp. 336-342.
Wang et al. "Highly efficient capture of circulating tumor cells by using nanostructured silicon substrates with integrated chaotic micromixers", Angewandte Chemmie International Edition, vol. 50, Issue 13, Mar. 4, 2011, pp. 3084-3088 (Mar. 4, 2011).
Wang et al. "Three-Dimensional Nanostructured Substrates toward Efficient Capture of Circulating Tumor Cells" Angewandte Chemie 121, 2009, pp. 9132-9135.
Wei et al. "The assembly of single-layer graphene oxide and graphene using molecular templates" Nano Letters, vol. 8, Aug. 2008, pp. 3141-3145, Aug. 2008.
Wendel et al., "Fluid biopsy for circulating tumor cell identification in patients with early-and late-stage non-small cell lung cancer: a glimpse into lung cancer biology", Physical Biology, vol. 9, 2012, pp. 1-9.
Wicha et al., Circulating tumor cells: not all detected cells are bad and not all bad cells are detected. Journal of Clinical Oncology: Official Journal of the American Society of Clinical Oncology, vol. 29, 2011, pp. 1508-1511.
Wikipedia, "Bovine serum albumin" http://en.wikipedia.org/wiki/Bovine_serum_albumin, retrieved Sep. 29, 2011, 1 Page.
Wikipedia, "Epithelial cell adhesion molecule" http://en.wikipedia.org/wiki/Epithelial_cell_adhesion_moledcule, retrieved Sep. 29, 2011, 1 Page.
Wikipedia, "Phosphate buffered saline" http://en.wikipedia.org/wiki/Phosphate_buffered_saline, retrieved Sep. 29, 2011, 1 page.
Willipinski-Stapelfeldt et al. "Changes in Cytoskeletal Protein Composition Indicative of an Epithelial-Mesenchymal Transition in Human Micrometastatic and Primary Breast Carcinoma Cells" Clinical Cancer Research 11, 2005, 2005, pp. 8006-8014.
Wu et al., "Preliminary investigation of the clinical significance of detecting circulating tumor cells enriched from lung cancer patients", Journal of Thoracic Oncology: Official Publication of the International Association for the Study of Lung Cancer, vol. 4, No. 1, 2009, pp. 30-36.
Xia et al. "An index for characterization of nanomaterials in biological systems" Nat Nano 5, 2010, pp. 671-675.
Xu et al. "Aptamer-based microfluidic device for enrinchment, sorting, and detection of multiple cancer cells" J. Analytical Chemistry, 81 (17), 2009, pp. 7436-7442.
Yoon et al. "Nanoassembly of graphene oxide for circulating tumor cell isolation" MicroTAS 2011 Conference, Oct. 2-6 2011, Seatle WA (www.microtas2011.org).
Yoon et al. "Sensitive capture of circulating tumour cells by functionalized graphene oxide nanosheets" Nature Nanotechnology vol. 8 (Oct. 2013), 8 pages.
Yoon et al. "Sensitive Detection of circulating tumor cells by graphene oxide nanoassembly" AIChE Annual Meeting 2011, Oct. 16-21, 2011, Minneapolis MN (www.aiche.org/Conferences/AnnualMeeting/index.aspx), 1 page.
Yu et al., "Circulating breast tumor cells exhibit dynamic changes in epithelial and mesenchymal composition", Science, vol. 339, Feb. 1, 2013, pp. 580-584.
Yu et al. "Circulating tumor cells: approaches to isolation and characterization" The Journal of Cell Biology 192, 2011, pp. 373-382.
Cogswell et al., "A Planar Labyrinth Micromixer", Proceedings of the 14th International Heat Transfer Conference IHTC14, Aug. 8-13, 2010, 5 pages.
U.S. Appl. No. 15/091,830, filed Apr. 6, 2016.
English language abstract for WO 2014/036951 extracted from espacenet.com database on May 25, 2016, 2 pages.
Aceto et al., "Circulating tumor cell clusters are oligoclonal precursors of breast cancer metastasis," Cell, 158, Aug. 28, 2014, pp. 1110-1122.
Aguirre-Ghiso et al., "Targeting dormant cancer," Nature Medicine, vol. 19, No. 3, Mar. 2013, pp. 276-277.
Alix-Panabieres et al., "Challenges in circulating tumour cell research", Nature Reviews, Cancer, vol. 14, Sep. 2014, pp. 623-631.
Baccelli et al., "Identification of a population of blood circulating tumor cells from breast cancer patients that initiates metastasis in a xenograft assay", Nature Biotechnology, vol. 31, No. 6, Jun. 2013, pp. 539-544.
Bhagat et al., "Pinched flow coupled shear-modulated inertial microfluidics for high-throughput rare blood cell separation", Lab on a Chip, The Royal Society of Chemistry, www.rsc.org/loc 2011, pp. 1870-1878.
Bissolati et al., "Portal vein-circulating tumor cells predict liver metastases in patients with resectable pancreatic cancer", Tumour Biology: The Journal of the International Society for Oncodevelopmental Biology and Medicine, 2015, pp. 991-996.
Brechot et al., "Circulating tumor cells (CTC) detection: Clinical impact and future directions", Science Direct, www.sciencedirect.com, 2006, pp. 180-204.
Carlsson et al., "Circulating tumor microemboli diagnostics for patients with non-small-cell lung cancer", Journal of Thoracic Oncology: Official Publication of the International Association for the Study of Lung Cancer, vol. 9, No. 8, Aug. 2014, pp. 1111-1119.
Dickson et al., "Efficient capture of circulating tumor cells with a novel immunocytochemical microfluidic device" AIP Biomicrofluidics, 2011, pp. 1-16.

(56) References Cited

OTHER PUBLICATIONS

Dharmasiri et al. "Highly efficient capture and enumeration of low abundance prostate cancer cells using prostate-specific membrane antigen aptamers immobilized to a polymeric microfluidic device", Electrophoresis, 2009, pp. 3289-3300.

Dong et al. "Microfluidics and Circulating Tumor Cells", The Journal of Molecular Diagnostics, 2012, pp. 1-9.

Fan et al. "Clinical significance of circulating tumor cells detected by an invasion assay in peripheral blood of patients with ovarian cancer", Gynecologic Oncology 112, 2009, pp. 185-191.

Funaki et al., "Novel approach for detection of isolated tumor cells in pulmonary vein using negative selection method: morphological classification and clinical implications", European Journal of Cardio-Thoracic Surgery: Official Journal of the European Association for Cardio-Thoracic Surgery, vol. 40, 2011, pp. 322-327.

Funaki et al., "Significance of tumour vessel invasion in determining the morphology of isolated tumour cells in the pulmonary vein in non-small-cell lung cancer", European Journal of Cardio-Thoracic Surgery: Official Journal of the European Association for Cardio-thoracic Surgery, vol. 43, 2013, pp. 1126-1130.

Haber et al., "Blood-based analyses of cancer: circulating tumor cells and circulating tumor DNA" Cancer Discovery, Jun. 2014, pp. 650-651.

Hashimoto et al., "Significant increase in circulating tumour cells in pulmonary venous blood during surgical manipulation in patients with primary lung cancer", Interactive Cardiovascular and Thoracic Surgery, vol. 18, 2014, pp. 775-783.

Hirsch et al., "Early detection of lung cancer: clinical perspectives of recent advances in biology and radiology", Clinical Cancer Research: An Official Journal of the American Association for Cancer Research, vol. 7, Jan. 2001, pp. 5-22.

Hoshino et al. "Microchip-based immunomagnetic detection of circulating tumor cells", Lab Chip, 2011, pp. 3449-3457.

Hou et al. "Capture and Stimulated Release of Circulating Tumor Cells on Polymer-Grafted Silicon Nanostructures", Advanced Materials, 2013, pp. 1547-1551.

Hou et al. "Circulating Tumor Cells as a Window on Metastasis Biology in Lung Cancer", The American Journal of Pathology, vol. 178, No. 3, Mar. 2011, pp. 989-996.

Hou et al., "Clinical significance and molecular characteristics of circulating tumor cells and circulating tumor microemboli in patients with small-cell lung cancer", Journal of Clinical Oncology: Official Journal of the American Society of Clinical Oncology, vol. 30, No. 5, Feb. 10, 2012, pp. 525-532.

Hou et al. "Isolation and retrieval of circulating tumor cells using centrifugal faces", Scientific Reports, 2013, pp. 1-8.

Iniesta et al., "Biological and clinical significance of MMP-2, MMP-9, TIMP-1 and TIMP-2 in non-small cell lung cancer", Oncology Reports, vol. 17, 2007, pp. 217-223.

Karabacak et al. "Microfluidic, marker-free isolation of circulating tumor cells from blood samples", Nature Protocols, vol. 9, No. 3, 2014, pp. 694-710.

Ke et al. "Programming Thermoresponsiveness of Nano Velcro Substrates Enables Effective Purification of Circulating Tumor Cells in Lung Cancer Patients", American Chemical Society, vol. 9, No. 1, 2015, pp. 62-70.

Khoja et al. "A pilot study to explore circulating tumour cells in pancreatic cancer as a novel biomarker" British Journal of Cancer, 2012, pp. 508-516.

Krebs et al., "Analysis of circulating tumor cells in patients with non-small cell lung cancer using epithelial marker-dependent and -independent approaches", Journal of Thoracic Oncology: Official Publication of the International Association for the Study of Lung Cancer, vol. 7, No. 2, 2012, pp. 306-315.

Koukourakis et al., "Enhanced expression of SPARC/osteonectin in the tumor-associated stroma of non-small cell lung cancer is correlated with markers of hypoxia/acidity and with poor prognosis of patients", Cancer Research, vol. 63, Sep. 1, 2003, pp. 5376-5380.

Lecharpentier et al., "Detection of circulating tumour cells with a hybrid (epithelial/mesenchymal) phenotype in patients with metastatic non-small cell lung cancer", British Journal of Cancer, vol. 105, 2011, pp. 1338-1341.

Lin et al. "Nanostructure Embedded Microchips for Detection, Isolation, and Characterization of Circulating Tumor Cells", Account of Chemical Research, 2014, pp. 2941-2950.

Liotta et al., "The significance of hematogenous tumor cell clumps in the metastatic process", Cancer Research, vol. 36, Mar. 1976, pp. 889-894.

Liu et al. "High throughout capture of circulating tumor cells using an integrated microfluidic system", Biosensors and Bioelectronics, 2013, pp. 113-119.

Livak et al., "Analysis of relative gene expression data using real-time quantitative PCR and the 2(-Delta Delta C(T)) Method", Methods, vol. 25, 2001, pp. 402-408.

Lortent-Tieulentet al., "International trends in lung cancer incidence by histological subtype: adenocarcinoma stabilizing in men but still increasing in women", Lung Cancer, vol. 84, 2014, pp. 13-22.

Luo et al., "Epithelial-mesenchymal plasticity of breast cancer stem cells: implications for metastasis and therapeutic resistance", Current Pharmaceutical Design, vol. 21, 2015, pp. 1301-1310.

Maheswaran et al., "Detection of Mutations in EGFR in Circulating Lung-Cancer Cells", The New England Journal of Medicine, Jul. 24, 2008, pp. 366-377.

Marrinucci et al., "Case study of the morphologic variation of circulating tumor cells", Human Pathology, vol. 38, 2007, pp. 514-519.

Marrinucci et al., "Cytomorphology of circulating colorectal tumor cells:a small case series", Journal of Oncology, Article I.D. 861341, 2010, pp. 1-7.

Mikolajczyk et al., "Detection of EpCAM-Negative and Cytokeratin-Negative Circulating Tumor Cells in Peripheral Blood", Journal of Oncology, 2011, pp. 1-10.

Miller et al. "Significance of Circulating Tumor Cells Detected by the Cellsearch System in Patients with Metastatic Breast Colorectal and Prostate Cancer", Journal of Oncology, Hindawi Publishing Corporation, vol. 2010, Article ID 617421, pp. 1-8.

Mittal et al. "Antibody-Functionalized Fluid-Permeable Surfaces for Rolling Cell Capture at High Flow Rates", Biophysical Journal, vol. 102, Feb. 2012, pp. 721-730.

Mittal et al. "Discontinuous Nanoporous Membranes Reduce Non-Specific Fouling for Immunoaffinity Cell Capture" Small, vol. 9, No. 24, 2013, pp. 4207-4214.

Murlidhar et al., "A radial flow microfluidic device for ultra-high-throughput affinity-based isolation of circulating tumor cells", Small, vol. 10, No. 23, 2014, pp. 4895-4904.

Nanguzgambo et al., Immunochemistry and lung cancer: application in diagnosis, prognosis and targeted therapy:, Oncology, vol. 80, 2011 pp. 247-256.

Okumura et al., "Circulating Tumor Cells in Pulmonary Venous Blood of Primary Lung Cancer Patients", The Annals of thoracic surgery, vol. 87, 2009, pp. 1669-1675.

Ozkumur et al. "Inertial Focusing for Tumor Antigen-Dependent and-Independent Sorting of Rare Circulating Tumor Cells", Science Translational Medicine, vol. 5, Issue 179, Apr. 3, 2013, pp. 1-11.

Pantel et al., "Functional Studies on Viable Circulating Tumor Cells", Clinical Chemistry, vol. 62, No. 2, 2015, pp. 328-334.

Peeters et al., "Circulating tumour cells and lung microvascular tumour cell retention in patients with metastatic breast and cervical cancer", Cancer Letters, vol. 356, 2015, pp. 872-879.

Pirozzi et al., "Prognostic value of cancer stem cells, epithelial-mesenchymal transition and circulating tumor cells in lung cancer", Oncology Reports, vol. 29, 2013, pp. 1763-1768.

Lu et al. "A Graphene Platform for Sensing Biomolecules" Angew Chem Int Ed Engl 48, 2009, pp. 4785-4787.

Maheswaran et al. "Detection of mutations in EGFR in circulating lung-cancer cells" The New England Journal of Medicine, vol. 359, Jul. 2008, pp. 366-377.

Mohanty et al. "Graphene-based single-bacterium resolution biodevice and DNA transistor: interfacing graphene derivatives with nanoscale and microscale biocomponents" Nano Lett 8, 2008, pp. 4469-4476.

(56) References Cited

OTHER PUBLICATIONS

Molloy et al. "The prognostic significance of tumour cell detection in the peripheral blood versus the bone marrow in 733 early-stage breast cancer patients" Breast Cancer Research 13, R61, 2011, 11 pages.
Mueller et al. "Prognostic impact of circulating tumor cells assessed with CellSearch System(TM) and AdnaTest Breast(TM) in metastatic breast cancer patients: the DETECT study" Breast Cancer Research 14:R118, 2012, 8 pages.
Nagrath et al. "Isolation of rare circulating tumour cells in cancer patients by microchip technology" Nature 450, 2007, pp. 1235-1239.
Nejlund et al. "In vitro detection of CTCs with the CytoTrack method", a poster presentation retrieved from www.cytotrack.dk/page12 on Apr. 16, 2014, 1 page.
Novoselov et al. "Two-dimensional gas of massless Dirac fermions in graphene" Nature, vol. 438, Issue 7065, Nov. 2005, pp. 197-200.
Nygaard et al. "Method comparison of CTC detection with CytoTrack and CellSearch", a poster presentation retrieved from www.cytotrack.dk/page12 on Apr. 16, 2014, 1 page.
Pantel et al. "Detection, clinical relevance and specific biological properties of disseminating tumour cells" Nat Rev Cancer 8, 2008, pp. 329-340.
Park et al. "Graphene oxide papers modified by divalent ions-enhancing mechanical properties via chemical cross-linking" ACS Nano 2, 2008, pp. 572-578.
Arya et al., "Enrichment, detection and clinical significance of circulating tumor cells", Lab on a Chip, 13, 2013, pp. 1995-2027.
Brongersma et al., "Plasmon-induced hot carrier science and technology", Nat. Nano. 10, 2015, pp. 25-34.
Cecchet et al., "One Step Growth of Protein Antifouling Surfaces: Monolayers of Poly(ethylene oxide) (PEO) Derivatives on Oxidized and Hydrogen-Passivated Silicon Surfaces", Langmuir: the ACS Journal of Surfaces and Colloids, 22, 2006, pp. 1173-1181.
Chaudhuri et al., "Myoblast differentiation of human mesenchymal stem cells on graphene oxide and electrospun graphene oxide-polymer composite fibrous meshes: importance of graphene oxide conductivity and dielectric constant on their biocompatibility", Biofabrication, 7, 2015, pp. 1-13.
Cunliffe et al., "Bacterial adsorption to thermoresponsive polymer surfaces", Biotechology Letters 22, 2000, pp. 141-145.
Das et al., "Graphene-Based Polymer Composites and Their Applications", Polymer-Plastics Technology and Engineering, 52, 2013, pp. 319-331.
Gupta et al., "Cancer Metastasis: Building a Framework", Massague, Cell 127, 2006, pp. 679-695.
Hatch et al., "Engineered Alginate Hydrogels for Effective Microfluidic Capture and Release of Endothelial Progenitor Cells from Whole Blood", Langmuir, 27, 2011, pp. 4257-4264.
Hoshino et al., "Preparation of a New Thermo-Responsive Adsorbent with Maltose as a Ligand and Its Application to Affinity Precipitation", Biotechnol Bioeng., 60, 1998, pp. 568-579.
Huber et al., "Programmed Adsorption and Release of Proteins in a Microfluidic Device", Science 301, 2003, pp. 352-355.
Hu et al., "Quantum-Dot-Tagged Reduced Graphene Oxide Nanocomposites for Bright Fluorescence Bioimaging and Photothermal Therapy Monitored in Situ", Advanced Materials, 24, 2012, pp. 1748-1754.
Ithimakin et al., "HER2 Drives Luminal Breast Cancer Stem Cells in the Absence of HER2 Amplification: Implications for Efficacy of Adjuvant Trastuzumab", Cancer Research, 73, 2013, pp. 1635-1646.
Kamande et al., "Modular Microsystem for the Isolation, Enumeration, and Phenotyping of Circulating Tumor Cells in Patients with Pancreatic Cancer", Analytical Chemistry 85, 2013, pp. 9092-9100.
Kim et al., "Graphene Oxide—Polyethylenimine Nanoconstruct as a Gene Delivery Vector and Bioimaging Tool", Bioconjugate Chemistry, 22, 2011, pp. 2558-2567.

Kumar et al., "Chemical Functionalization of Graphene to Augment Stem Cell Osteogenesis and Inhibit Biofilm Formation on Polymer Composites for Orthopedic Applications", ACS Applied Materials & Interfaces, 7, 2015, pp. 3237-3252.
Li et al., "Organo- and Water-Dispersible Graphene Oxide—Polymer Nanosheets for Organic Electronic Memory and Gold Nanocomposites", Journal of Physical Chemistry C, 114, 2010, p. 12742-12748.
Liu et al., "Hydrophobic Interaction-Mediated Capture and Release of Cancer Cells on Thermoresponsive Nanostructured Surfaces", Advanced Materials 25, 2013, pp. 922-927.
Maheswaran et al., "Circulating tumor cells: a window into cancer biology and metastasis", Current Opinion in Genetics & Development 20, 2010, pp. 96-99.
Nakamura et al., "Uptake and release of budesonide from mucoadhesive, pH-sensitive copolymers and their application to nasal delivery", Journal of Controlled Release 61, 1999, pp. 329-335.
Nitschke et al., "Thermo-responsive poly(NiPAAm-co-DEGMA) substrates for gentle harvest of human corneal endothelial cell sheets", Journal of Biomedical Materials Research Part A, 80A, 2007, pp. 1003-1010.
Pant et al., "Processing and characterization of electrospun graphene oxide/polyurethane composite nanofibers for stent coating", Chemical Engineering Journal, 270, 2015, pp. 336-342.
Paterlini-Brechot et al., "Circulating tumor cells (CTC) detection: Clinical impact and future directions", Cancer Letters 253, 2007, pp. 180-204.
Reategui et al., "Tunable Nanostructured Coating for the Capture and Selective Release of Viable Circulating Tumor Cells", Adv. Mater, 27, 2015, pp. 1593-1599.
Sahoo et al., "Functionalized carbon nanomaterials as nanocarriers for loading and delivery of a poorly water-soluble anticancer drug: a comparative study", Chemical Communications, 47, 2011, pp. 5235-5237.
Stile et al., "Thermo-Responsive Peptide-Modified Hydrogels for Tissue Regeneration", Biomacromolecules, 2, 2001, pp. 185-194.
Sun et al., "Nano-Graphene Oxide for Cellular Imaging and Drug Delivery", Nano Research 1, 2008, pp. 203-212.
Thampi et al., "Mechanical characterization of high-performance graphene oxide incorporated aligned fibroporous poly(carbonate urethane) membrane for potential biomedical applications", Journal of Applied Polymer Science, 2015, pp. 132-139.
Wang et al., "Nanostructured substrates for isolation of circulating tumor cells", Nano Today 8, 2013, pp. 374-387.
Wu et al., "Supercapacitors Based on Flexible Graphene/Polyaniline Nanofiber Composite Films", ACS Nano, 4, 2010, pp. 1963-1970.
Yoon et al., "Emerging Role of Nanomaterials in Circulating Tumor Cell Isolation and Analysis", ACS Nano 8, 2014, pp. 1995-2017.
Zhang et al., "Microfluidics and cancer: are we there yet?", Biomedical Microdevices 15, 2013, pp. 595-609.
Zhuang et al., "Conjugated-Polymer-Functionalized Graphene Oxide: Synthesis and Nonvolatile Rewritable Memory Effect", Adv. Mater., 22, 2010, pp. 1731-1735.
Bhagat et al., Inertial Microfluidics for Continuous Particle Filtration and Extraction, Microfluidics and Nanofluidics, vol. 7, No. 2, 2008, pp. 217-226.
Gossett et al., "Label-Free Cell Separation and Sorting in Microfluidic Systems", Analytical and Bioanalytical Chemistry, vol. 397, No. 8, 2010, pp. 3249-3267.
Kuntaegowdanahalli et al., "Inertial Microfluidics for Continuous Particle Separation in Spiral Microchannels", Lab on a Chip, vol. 9, 2009, pp. 2973-2980.
Vancoillie, Gertjan et al., "Thermoresponsive Poly(oligo ethylene glycol acrylates)", Progress in Polymer Science, vol. 39, 2014, pp. 1074-1095.

* cited by examiner

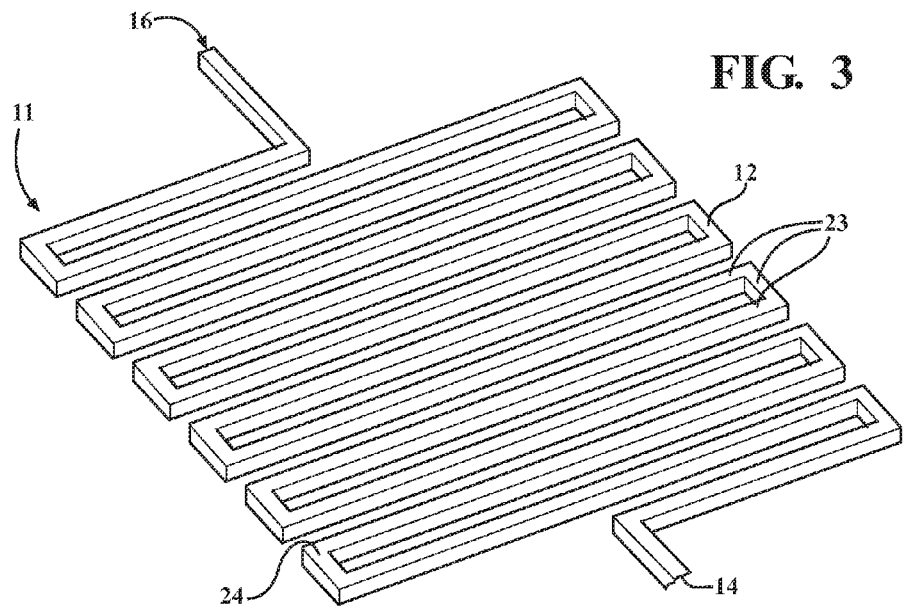
FIG. 3
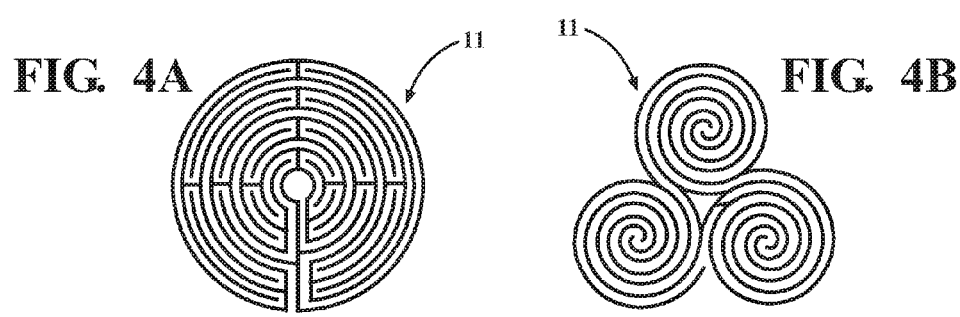
FIG. 4A
FIG. 4B
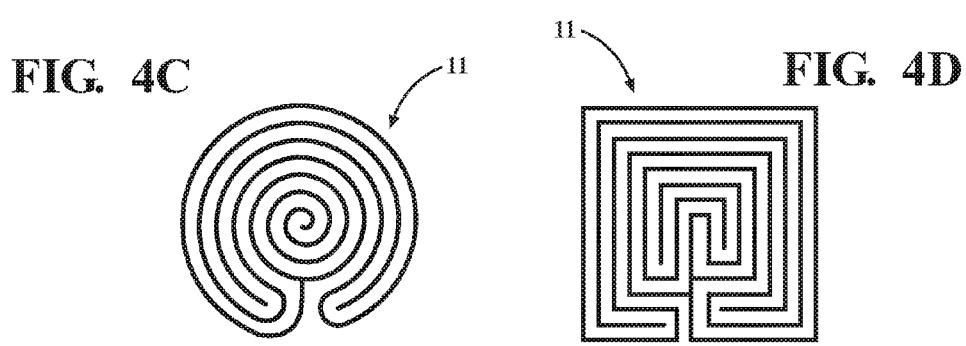
FIG. 4C
FIG. 4D

FIG. 4E 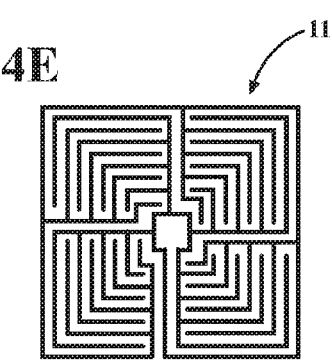 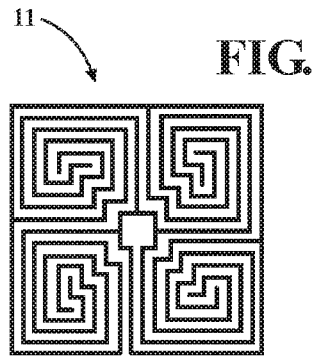 FIG. 4F
FIG. 4G 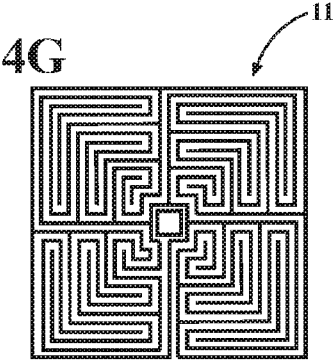 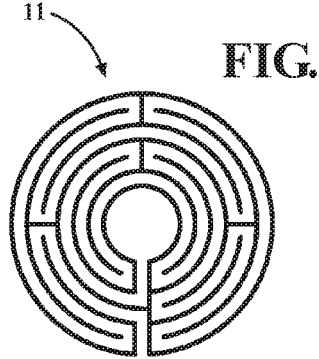 FIG. 4H
FIG. 4I 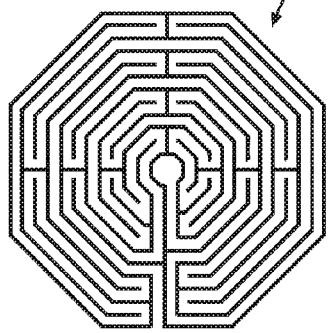 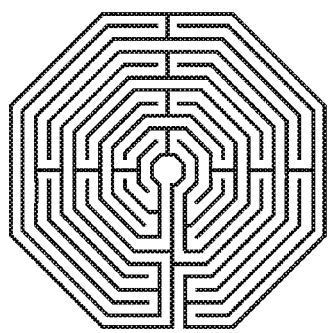 FIG. 4J

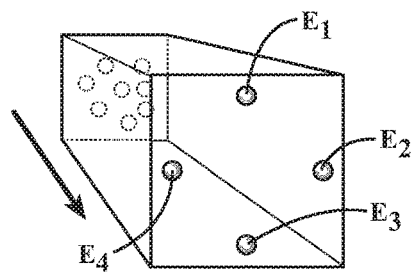
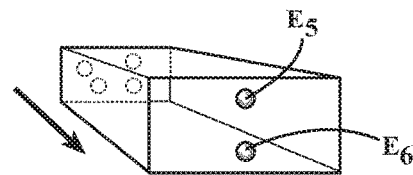
FIG. 6A  FIG. 6B
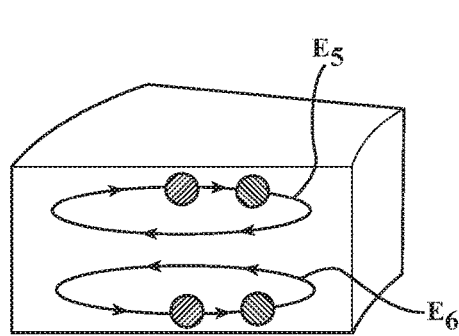
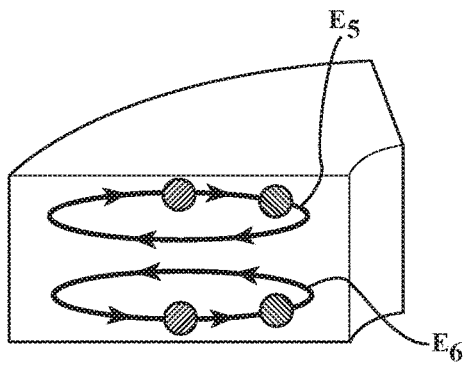
FIG. 7A  FIG. 7B
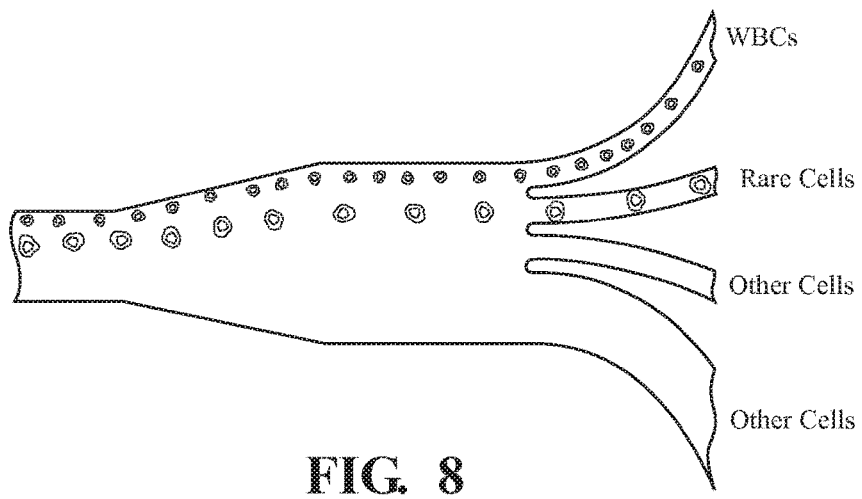
FIG. 8

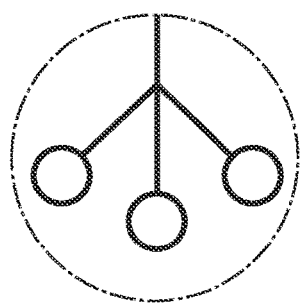
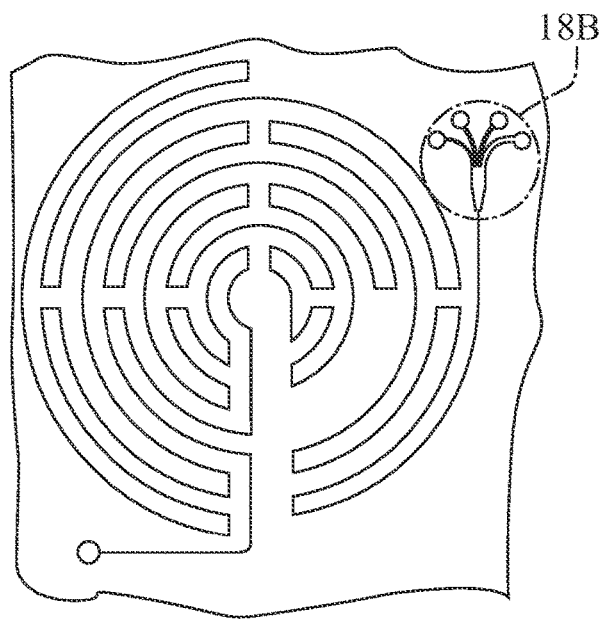
FIG. 17B                FIG. 18A
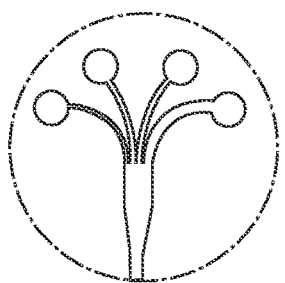
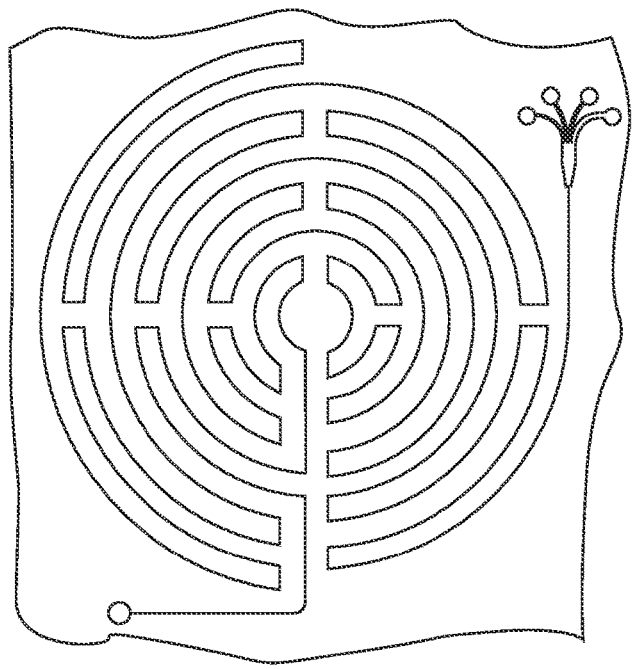
FIG. 18B                FIG. 19

MICROFLUIDIC DEVICE AND METHOD FOR DETECTING RARE CELLS

RELATED APPLICATIONS

The subject patent application is the National Stage of International Patent Application No. PCT/US2013/067315, filed on Oct. 29, 2013, which claims priority to and all the advantages of U.S. Provisional Application Ser. No. 61/795,860 filed on Oct. 29, 2012, the content of which is incorporated herein by reference.

FIELD OF THE DISCLOSURE

The present disclose relates generally to microfluidics and, more particularly, to a method for detecting rare cells utilizing a microfluidic device.

BACKGROUND

As is well appreciated in the art, there are myriad technological obstacles in the identification, enumeration, detection, capture, and isolation of rare cells. These technological obstacles tend to limit the quantitative evaluation of rare cells, for example, in early diagnosis of metastatic diseases and effective monitoring of therapeutic response in patients. Some rare cells, e.g. circulating tumor cells (CTCs) and/or viable tumor-derived epithelial cells, are identified in peripheral blood from cancer patients and are likely the origin of intractable metastatic disease. CTCs, as just one type of rare cell, tend to be present in an amount of about 1 CTC per 1 billion blood cells and tend to circulate in peripheral blood of patients with metastatic cancer. Detection, isolation, and capture of CTCs represent a potential alternative to invasive biopsies during diagnosis of disease. More specifically, the ability to identify, isolate, propagate and molecularly characterize CTC subpopulations could further the discovery of cancer stem cell biomarkers, expand the understanding of the biology of metastasis, and improve the therapeutic treatment of cancer patients and the ultimate treatment outcome. Many current strategies for isolating CTCs are limited to complex analytic approaches that are typically very low yield and/or low purity.

Many existing technologies for capturing CTCs utilize size based separation techniques. For example, CTCs derived from solid tumors tend to be larger in size compared to typical red blood cells. For this reason, techniques have emerged wherein CTCs are passed through pores etched in membranes wherein the CTCs are trapped on the membrane. However, these techniques tend to suffer from clogging of the pores and pressure drops in devices that include such membranes due to collection of cells on the membranes. In addition, the viscoelastic properties of CTCs allow such cells to squeeze, or be pushed, through the pores. For this reason, related techniques have resorted to pre-fixation of the cells. However, one of the major limitations associated with pre-fixation is adequate throughput and excessive non-specific cell retention. Although processing speeds of such methods tend to be efficient compared to immunoaffinity capture based methods, the amounts of samples that can be processed without sacrificing efficiency and purity is limited. Accordingly, there remains an opportunity to develop an improved method and device for detecting rare cells.

SUMMARY

This disclosure provides a microfluidic device for detecting rare cells in a fluid sample that includes the rare cell and other cells. The microfluidic device comprises an inlet for receiving the fluid sample, a labyrinth channel structure in fluid communication with the inlet, and an outlet in fluid communication with the labyrinth channel structure for collecting the rare cells separated from the other cells in the fluid sample. The labyrinth channel structure comprises at least one channel through which the fluid sample flows. The at least one channel has a plurality of segments and a plurality of corners with each corner defined between adjacent segments. The presence of the plurality of corners induces separation of the rare cells from the other cells in the fluid sample as the rare cells move to a first equilibrium position within the at least one channel when a ratio of inertial lift forces ($F_z$) and Dean flow ($F_D$) of the fluid sample is from 2 to 10.

A method for detecting rare cells is also disclosed herein. The method comprises providing a microfluidic device comprising an inlet, a labyrinth channel structure in fluid communication with the inlet and comprising at least one channel having a plurality of segments and a plurality of corners with each corner defined between adjacent segments, and an outlet in fluid communication with the at least one channel. The method further comprises introducing the fluid sample into the inlet of the microfluidic device, flowing the fluid sample through the labyrinth channel structure, and separating the rare cells from the other cells in the fluid sample as the fluid sample flows past the plurality of corners in the at least one channel of the labyrinth channel structure. The rare cells move to a first equilibrium position within the at least one channel when a ratio of inertial lift forces ($F_z$) and Dean flow ($F_D$) of the fluid sample is from 2 to 10.

BRIEF DESCRIPTION OF THE DRAWINGS

Other advantages of the present disclosure is readily appreciated, as the present disclosure becomes better understood by reference to the following detailed description when considered in connection with the accompanying drawings.

FIG. 3 is a perspective view of the channel(s) of a microfluidic device according to another embodiment of the present disclosure FIGS. 4A through 4K are top views of the channel(s) of still other embodiments of the microfluidic device.

FIGS. 6A and 6B are schematic cross sections of a microfluidic device including a straight channel that illustrates cells focused at four equilibrium positions in the square channel (FIG. 6A) and at two equilibrium positions in the rectangular channel (FIG. 6B) due to inertial lift force.

FIGS. 7A and 7B are schematic diagrams showing the effect of Dean How in cell focusing.

FIG. 8 is a schematic diagram of an outlet of the microfluidic device.

FIGS. 17A and 17B are schematic diagrams showing still another example of microfluidic device (FIG. 17A) having an outlet design (FIG. 17B) for the separation of cells to collect cells based on size.

FIGS. 18A and 18B are schematic diagrams showing another example of microfluidic device (FIG. 18A) having an outlet design (FIG. 18B) for the separation of cells to collect cells based on size.

FIG. 19 is a schematic diagram showing still another example of a microfluidic device having an outlet design for the separation of cells to collect cells based on size.

DETAILED DESCRIPTION OF THE DISCLOSURE

Figure 1:
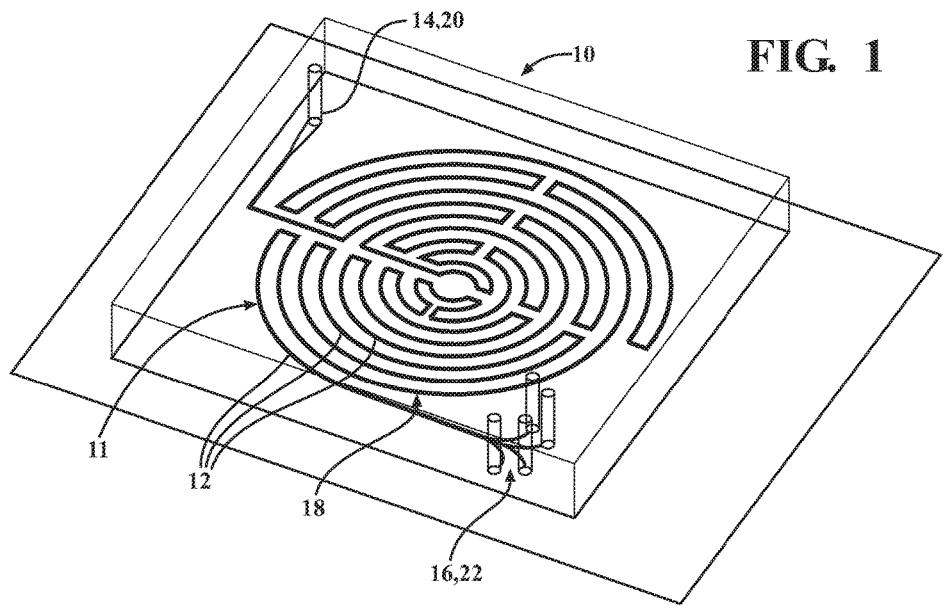
FIG. 1 is a perspective view of a microfluidic device according to an embodiment of the present disclosure.

The present disclosure provides a microfluidic device 10, and a method for detecting rare cells (using the microfluidic device 10). Most typically, the rare cells are present in samples of blood, e.g. anticoagulated whole blood. However, it is also contemplated that the rare cells may be present in samples of other bodily fluids that may be, include, consist essentially of, or consist of, but are not limited to, saliva, mucus, excretions, and the like. The terminology "consist essentially of" describes an embodiment wherein the bodily fluid is not diluted with a diluent. In one embodiment, the rare cells may be transmitted via breath, i.e., breathing, sneezing, coughing, and the like, such that the rare cells may be, at least for a time, airborne and thus still be present in a bodily fluid for purposes of this disclosure. The bodily fluid may be utilized without pre-dilution, pre-labeling, pre-fixation, centrifugation, lysis, or any other processing steps.

Transporting fluids, such as buffers, which may be miscible or immiscible with various samples of blood and/or bodily fluids, may also be employed. In various embodiments, samples of blood, bodily fluids, and the like, may be evaluated in volumes of about 500 µL to about 5 mL, about 100 µL to about 1 mL, or about 250 µL to about 550 µL. However, the present disclosure is not limited to these volumes or to dilution of bodily fluids. In one embodiment, about 1 mL of sample is utilized. In other embodiments, 1 to 20, 2 to 19, 3 to 18, 4 to 17, 5 to 16, 6 to 15, 7 to 14, 8 to 13, 9 to 12, or 10 to 11, mL of sample are utilized. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

The particular type of rare cells contemplated in this disclosure is not limited. In one embodiment, the rare cells are further defined as circulating tumor cells (CTCs), such as semi-mesenchymal phenotype cells, semi-epithelial/mesenchymal phenotype cells and/or epithelial phenotype cells. In another embodiment, the rare cells the rare cells are defined as a combination of CTCs and circulating cancer stem cells (CCSCs). CCSCs are a sub-population of CTCs. In yet other embodiments, the rare cells are chosen from the group of endothelial cells, fetal cells, and/or cells of hemopoietic origin (e.g. platelets, sickle cell red blood cells, and sub-populations of leukocytes). In still other embodiments, the terminology "rare cells" alternatively describes exosomes, microvessicles, bacteria, viruses, protists, and/or fungi.

The rare cells, such as CTCs, may be present, for example in blood, bodily fluids, and the like, in any amount, e.g. in amounts of from 0.01 to 10, from 0.1 to 10, from 1 to 10, from 1 to 20, from 1 to 30, from 1 to 40, from 1 to 50, from 1 to 60, from 1 to 70, from 1 to 80, from 1 to 90, from 1 to 100, from 100 to 1000, from 200 to 900, from 300 to 800, from 400 to 700, from 500 to 600, from 1 to 5, or 0.1, 0.2, 0.3, 0.4, 0.5, 0.6, 0.7, 0.8, 0.9, 1, 2, 3, 4, 5, 6, 7, 8, 9, or 10, rare cells per one billion total blood cells. Alternatively, the rare cells may be present in amounts of greater than 0.01, 0.1, 1, 10, 50, 100, 500, 1000, 5000, or 10000, rare cells per one billion total blood cells. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments. Rare cells present in bodily fluids other than blood and/or CTCs may also be present in the aforementioned amounts. However, the instant disclosure is not limited to these amounts of rare cells present in bodily fluids and it is contemplated that higher or lower amounts may also be utilized.

Method of Detecting Rare Cells:

A method for detecting rare cells generally applies inertial migration of particles to achieve high throughput particle separation based, at least in part, on particle size. Utilizing the principles of hydrodynamic separation, a microfluidic device 10 having a labyrinth channel structure, which is described in detail below, may be used to achieve the high throughput separation of cells (e.g. CTCs). A non-limiting embodiment of one such microfluidic device 10 is shown in FIG. 1. In one embodiment, the microfluidic device 10 has a complex channel geometry that generally ensures that various sized cells in a fluid sample (e.g., a bodily fluid such as blood) can be effectively and efficiently focused and separated, e.g. at 1 to 2 mL/min, by flowing through the channel structure. Additionally, high purity and high recovery of rare cells (e.g. CTCs or a combination of CTCs and CCSCs) may be obtained such that the cells may be collected for further isolation and analysis.

The method also allows for small amounts of a fluid sample (e.g. a bodily fluid) to be evaluated accurately and precisely and in a time and cost effective manner to determine the presence of the rare cells. The method also allows for the separation of the rare cells from other cells (e.g. white blood cells (WBC), red blood cells (RBC), and platelets) in the fluid sample with high recovery and specificity.

One embodiment of the method for detecting rare cells comprises the steps of providing a microfluidic device 10, introducing a fluid sample to an inlet 14 of the microfluidic device 10, flowing the fluid sample through a channel structure (e.g. a labyrinth channel structure 11) of the microfluidic device 10, and separating the rare cells from other cells in the fluid sample. The separation of the rare cells may be defined as detection, identification, isolation, separation, and/or enumeration of the rare cells.

The step of providing the microfluidic device 10 is not particularly limited and may be further defined as building or constructing the microfluidic device 10 or obtaining the microfluidic device 10 by any other mechanism. The step of introducing the fluid sample is also not particularly limited. Typically, this step is further defined as exposing the microfluidic device 10 to the fluid sample such that the fluid sample flows in and/or through the microfluidic device 10. In one embodiment, the step of introducing the fluid sample is further defined as injecting or adding the fluid sample to an input of the microfluidic device 10. The method may also include the step of flowing the fluid sample through the microfluidic device 10, e.g. along or through a microfluidic channel 12 to an outlet 16.

The fluid sample may be introduced by any method for example, by injecting. The step of introducing may be continuous or discontinuous. The fluid sample may be introduced to the microfluidic device 10 in any amount and pressure. Typically, the maximum shear force exerted on a cell, based on a volumetric flow rate of about 1 mL/h, is about 0.4 dynes/cm$^2$ at θ=68°, and the maximum velocity is about 460 µm/s. The shear stress produced by introducing the fluid sample to the microfluidic device 10 is typically of from about 0.1 to about 20 dyn/cm$^2$ and may be less than 15, 10, 5, 1, or 0.5, dyn/cm$^2$. Shear stress is not necessarily constant. In other embodiments, the fluid sample may be introduced at a rate of 0.1 L to 30 mL/hr. Typical flow rates are typically from 0.5 to 1, from 1 to 20, 2 to 19, 3 to 18, 4 to 17, 5 to 16, 6 to 15, 7 to 14, 8 to 13, 9 to 12, or 10 to 11, mL/hr. However, these rates are not limiting and the rate at which the sample passes through may be greater or less than those described above. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

The step of flowing the fluid sample through the channel structure 11 of the microfluidic device 10 is also not particularly limited. The flowing of the fluid sample may be continuous or discontinuous based, at least in part, on how the fluid sample is introduced to the inlet 14 of the microfluidic device 10. Additionally, the fluid sample flows through the channel structure 11 at substantially the same rate at which the fluid sample is introduced to the inlet 14 of the microfluidic device 10.

The step of separating the rare cells from the other cells in the fluid sample occurs during the flowing of the fluid sample through the channel structure 11 of the microfluidic device 10. In one embodiment, the step of separating the rare cells occurs as the fluid sample flows such that the rare cells are separated based on one or more physical forces, such as Dean Forces. Alternatively, the step of separating may be described as harvesting the rare cells and/or physically removing the rare cells from the microfluidic device 10.

For example, and as is described in further detail below, as the fluid sample flows through the channel structure 11, the rare cells move, migrate, or reposition themselves to a first equilibrium position (e.g. equilibrium position $E_1$ shown in FIG. 6A) within the channel(s) 12 of the channel structure 11. Movement, migration, repositioning or the like of the rare cells occurs when a ratio of inertial lift forces ($F_z$) and Dean flow ($F_D$) of the fluid sample is, e.g. from 2 to 10. Further details of the movement, migration, repositioning or the like of the rare cells are described below with reference at least to FIGS. 5-15.

Microfluidic Device:

Embodiments of the microfluidic device 10 will now be described. The microfluidic device may be, include, consist essentially of, or consist of, a metal, plastic, polymer, inorganic compound, glass, silicon (e.g. —Si—Si—), silicone (e.g. —Si—O—Si— or PDMS), epoxy, semiconductor, and/or combinations thereof. In various embodiments, the terminology "consist essentially of" or the like typically describes that the microfluidic device 10 as including one or more of the particular aforementioned materials and is free of, or includes less than 0.1 or 1, weight percent, of dissimilar materials. The microfluidic device 10 may be fabricated using any technique known in the art including, but not limited to, molding, photolithography, electroforming, machining, chemical vapor deposition, and the like.

In various embodiments, the microfluidic device 10 is, includes, consists essentially of, or consists of, polydimethylsiloxane (PDMS). Alternatively, the microfluidic device 10 may be, include, consist essentially of, or consist of, a different silicone polymer, an organic polymer, e.g. polyethylene terephthalate (PET), polyimide, polyether ether ketone (PEEK), and/or combinations thereof.

The microfluidic device 10 is not particularly limited in dimensions. Suitable non-limiting examples of microfluidic devices 10 have one or more dimensions (e.g. length, width, and/or height) on the scale of 1 to 100, 1 to 75, 1 to 50, 1 to 25, 1 to 20, 1 to 15, 1 to 10, 1 to 5, or 0.1 to 1, inches, centimeters, and/or millimeters. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

One non-limiting embodiment of the microfluidic device 10 is shown in FIG. 1. The microfluidic device 10 generally includes one or more microfluidic channels 12 forming a channel structure 11, an inlet 14, and an outlet 16. While the embodiments described herein have microfluidic channels 12, it is to be understood that larger devices typically include microfluidic chambers as opposed to microfluidic channels 12. It is further to be understood that this is not necessarily true in every embodiment. Additionally, the channel 12 may otherwise be a tube, a tunnel, an artery, a chamber, a conduit, a passage, a pipe, or the like.

The microfluidic channels 12 are designed to allow blood, body fluids, and/or other substances can flow through them. Said differently, the microfluidic device 10 may include a single microfluidic channel 12, two microfluidic channels 12, or three or more (i.e., a plurality of) microfluidic channels 12, thereby forming the channel structure 11. Each individual microfluidic channel 12 may be used to isolate one or more types of rare cells.

In various embodiments, the fluid sample is a sample of blood, bodily fluid, or the like, and is segmented into two or more segments. The segments flow through different microfluidic channels 12 at one or more pressures and/or velocities. In one embodiment, the microfluidic device 10 has one or more microfluidic channels 12, one or more of which independently have a length, height, and/or width of from 1 µm to 1000 µm (i.e., 1 mm). In various embodiments, one or more of these values is from 1 µm to 100, 5 to 95, 10 to 90, 15 to 85, 20 to 80, 25 to 75, 30 to 70, 35 to 65, 40 to 60, 45 to 55, or 50 to 55, µm. In other embodiments, one or more of these values is from 100 to 1000, from 125 to 975, from 150 to 950, from 175 to 925, from 200 to 900, from 225 to 875, from 250 to 850, from 275 to 825, from 300 to 800, from 325 to 775, from 350 to 750, from 375 to 725, from 400 to 700, from 425 to 675, from 450 to 650, from 475 to 625, from 500 to 600, from 525 to 575, or from 550 to 575, µm. In other embodiments, the width may be up to 5 mm, and the length up to 100 to 1000 mm. The dimensions of the microfluidic device 10, as a whole, are not particularly limited. In various embodiments, any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

The volume of the microfluidic channel 12 may be customized depending on a volume of the fluid sample used. The volume of the microfluidic channel 12 may be smaller or larger than the size of the sample or may be approximately the same as the size of the sample. In various embodiments, the microfluidic device 10 and/or the microfluidic channel 12 has a volume of from about 100 µL to 20 mL, from about 100 µL, to 15 mL, from about 100 µL to 10 mL, from about 100 µL to 5 mL, from about 100 µL to 1 mL, or from about 100 µL to 0.5 mL. However, these volumes are not limiting, and the volume of the microfluidic device 10 and/or the microfluidic channel 12 may be greater or less than those described above. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

One of more microfluidic channels 12 of the channel structure 11 may individually have a unique shape and/or structure. For instance, the channel structure 11 may have channel(s) 12 with a rounded shape and/or structure. This is shown, for example, in FIGS. 1 and 2. The channel structure 11 may otherwise have channel(s) 12 with a straight shape and/or structure. This is shown, for example, in FIG. 3. In addition, the channel structure 11 may have one or more microfluidic channels 12 that has a shape or pattern that is different from any one or more other microfluidic channels 12 in the same microfluidic device 10. In one embodiment, the geometry of these patterns (i.e., of the one or more microfluidic channels 12) is described as a labyrinth pattern, in whole or in part. In one embodiment, the geometry of the patterns may be described as a labyrinth pattern, a maze, or a regular or an irregular network of channels. The channel(s) 12 may also be single, non-branching path, which leads from the edge or inlet 14 to the center or the outlet 16. Various non-limiting examples of suitable patterns of the channel structure 11 are set forth in FIGS. 4A through 4K.

Referring back to FIG. 1, the microfluidic device 10 may have a central body 18, a longitudinal axis, and upstream 20 and downstream 22 ends opposite each other. The central body 18 may define the microfluidic channel 12 which is in fluid communication with the upstream 20 and downstream 22 ends along the longitudinal axis for receiving the fluid sample. The microfluidic device 10 may also include an entrance (e.g. inlet 14) defined by the central body 18 and disposed at the upstream end 20 of the central body 18. Furthermore, the microfluidic device 10 typically includes an exit (e.g. outlet 16) also defined by the central body 18 and disposed at the downstream end 22 of the central body 18. Both the entrance and exit are typically disposed transverse to the longitudinal axis. The geometry of the microfluidic channel 12 is not particularly limited but may be designed to increase or decrease flow through, velocity through, or pressure in, the microfluidic channel 12.

The microfluidic device 10 may be designed to allow for optical or visual inspection of the microfluidic channels 12. For example, the microfluidic device 10 may include a top, bottom, and/or side which may be transparent, approximately transparent, or see-through to allow for optical or visual inspection. Alternatively, the microfluidic device 10 may include a top, bottom, and/or side which may be opaque. It is also contemplated that the microfluidic device 10 may not include a top. In addition, the microfluidic device 10 may be designed to maximize efficiency relative to flow, velocity and/or shear force of a fluid sample passing therethrough.

The microfluidic channel 12 may be modified to increase surface area, volume, etc. to increase a probability that a rare cell is captured. For example, when the walls of the channel 12 are substantially planar, the height of the microfluidic channel 12 may be designed so that rare cells are more efficiently detected and/or trapped.

The microfluidic device 10 is not particularly limited to any particular efficiency. However, in various embodiments, the microfluidic device 10 can typically identify, enumerate, detect, capture, and/or isolate from 1 to 10,000, 1 to 7,500, 1 to 5,000, 1 to 2,500, 1 to 1500, from 5 to 1000, from 10 to 500, from 25 to 200, or from 50 to 100, rare cells from a blood sample of about 1 mL or less. Alternatively, the microfluidic device 10 may have a rare cell capture efficiency of at least 1, 5, 10, 15, 20, 25, 30, 35, 40, 45, 50, 55, 60, 65, 70, 75, 80, 85, 90, 95, or 99, percent determined as (rare cells captured or isolated in the microfluidic device 10 divided by a total number of rare cells introduced to the microfluidic device 10 multiplied by 100. In other embodiments, the microfluidic device 10 may have a rare cell capture efficiency of 95 to 100, 90 to 95, 90 to 100, 85 to 95, 85 to 90, 80 to 85, 80 to 90, 80 to 95, 75 to 80, 75 to 85, 75 to 90, 75, to 95, 70 to 75, 70 to 80, 70 to 85, 70 to 90, 75 to 95, 50 to 95, 55 to 90, 60 to 85, 65 to 80, 65 to 75, 65 to 70, 25 to 50, 59 to 75, or 25 to 75, percent, as determined using the formula described immediately above. In various embodiments, the microfluidic device 10 has a rare cell capture efficiency of about 70, 75, or 80 plus or minus about 20, 25, or 30, at 5-20 cells/mL spiked in blood. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

The microfluidic device 10 may allow captured cells to be grown and cultivated and/or washed such that non-specifically bound cells, e.g., leukocytes, may be removed which may result in about a $10^6$-fold enrichment. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

The microfluidic device 10 typically includes the inlet 14, e.g. an inlet 14 port, for receiving the fluid sample, a channel structure 11 in fluid communication with the inlet 14 and comprising at least one channel 12 through which the fluid sample flows, and the outlet 16, e.g. an outlet 16 port, in fluid communication with the at least one channel 12 for collecting the rare cells separated from other cells (e.g. white blood cells, red blood cells, platelets, etc.) in the fluid sample. In various embodiments, the microfluidic device 10 includes a single entrance and a single exit. In one embodiment, one or more channels 12 is/are disposed between and are fluidly connected to the inlet 14 and the outlet 16. The channel(s) 12 make up the channel structure 11 and may be disposed in any pattern, e.g. a labyrinth pattern or more than one labyrinth pattern. In these instances, the channel structure 11 is referred to as a labyrinth channel structure 11.

The labyrinth channel structure 11 generally comprises at least one channel 12 having a plurality of segments 23 and a plurality of corners 24. This is shown, for example, in FIGS. 2 and 3. Each corner 24 is typically defined between adjacent segments 23. Without intending to be bound by any particular theory, it is believed that the combination of various factors within the channel structure 11, such as inertial focusing, Dean Flow, and numerous corners 24, is responsible for separation of the rare cells from other cells in the fluid sample. For instance, the presence of numerous corners 24 typically induces separation of the rare cells from other cells in the fluid sample as the rare cells move to a first equilibrium position (e.g. E1 shown in FIG. 6A) within the channel(s) 12 when a ratio of inertial lift forces ($F_Z$) and Dean flow ($F_D$) of the fluid sample is, e.g. from 2 to 10.

Figure 5:
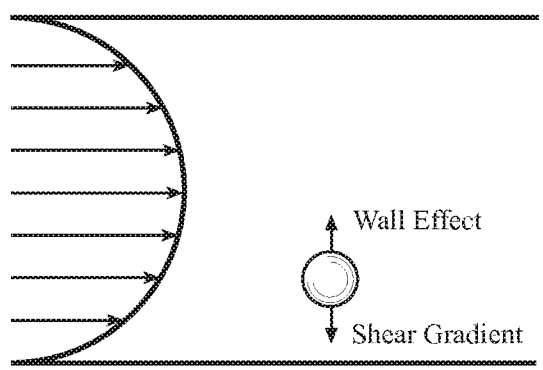
FIG. 5 is a schematic diagram showing the lift force balance between shear gradient and wall effect in a microfluidic channel.
Figure 9A:
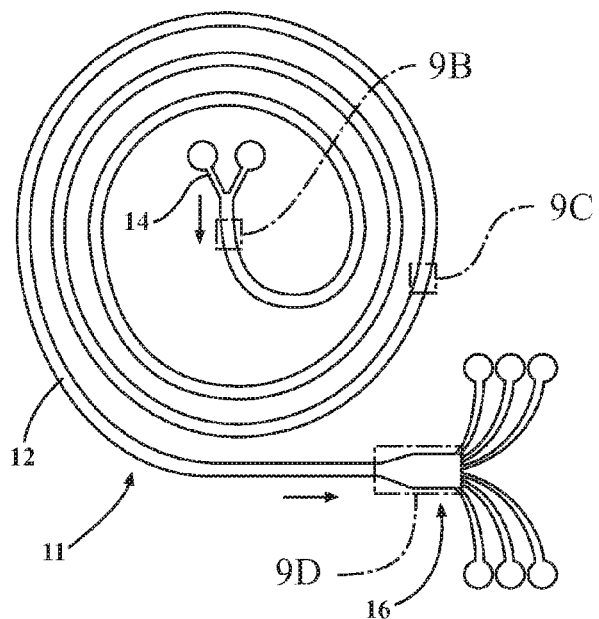
FIG. 9A is a schematic diagram of an example of a microfluidic device.
Figure 9B:
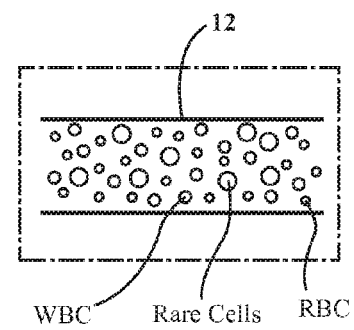
FIG. 9B is a schematic cross section of a channel of the microfluidic device of FIG. 9A near an inlet.
Figure 9C:
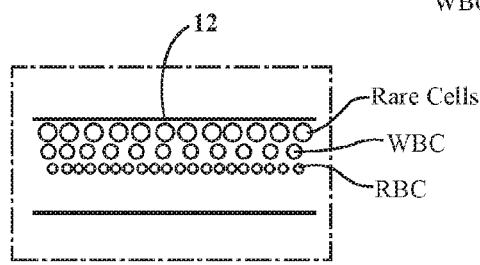
FIG. 9C is a schematic cross section of a channel of the microfluidic device of FIG. 9A during separation of the cells.
Figure 9D:
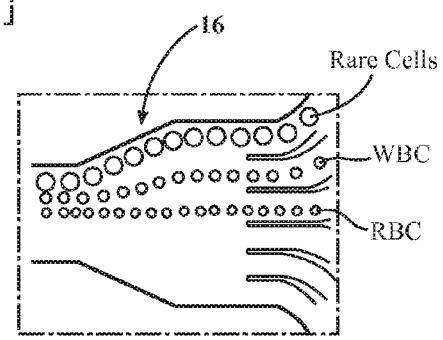
FIG. 9D is a schematic cross section of a channel of the microfluidic device of FIG. 9A at the outlet.

More specifically, it is believed that the phenomenon of inertial focusing may operate in the instant method and microfluidic device 10 and contribute to detection of rare cells. For example, when fluid samples (such as bodily fluids) are introduced into a microfluidic device 10, inertial migration based cell separation typically relies on equilibrium between inertial lift forces and Dean flow that results in the migration of particles, e.g. cells, in laminar microfluidic devices 10 with a curved channel(s) 12. Cells in a straight channel typically experience stresses that act over the surface of the bodily fluid, including the shear stress that yield drag forces and the normal stress that yields lift forces to the direction of main flow. With reference to FIGS. 5, 6A, and 6B, cells may be maintained at specific positions due to the inertial lift forces combined by a shear gradient lift that pushes the cells through the wall and the wall lift effect that pushes the cells through the center. For instance, FIG. 6A shows that there are four equilibrium positions ($E_1$, $E_2$, $E_3$, $E_4$) typically present in a square channel, and FIG. 6B shows that there are two equilibrium positions ($E_5$, $E_6$) typically present in a rectangular channel. The inertial lift forces tend to cause cells in a straight channel to be confined in several positions, where the number of equilibrium points is related to the geometry of the channel 12.

When the rare cells are separated from the other cells in the fluid sample, the rare cells typically move to one of the equilibrium positions $E_1$, $E_2$, $E_3$, $E_4$ in a square channel or one of the equilibrium positions $E_5$, $E_6$ in a rectangular channel. When this occurs, the rare cells typically form a stream of rare cells. Likewise, WBCs in the fluid sample typically also separate from the rare cells and the remaining other cells to one of the equilibrium positions $E_1$, $E_2$, $E_3$, $E_4$ in a square channel or one of the equilibrium positions $E_5$, $E_6$ in a rectangular channel. The WBCs typically also form a stream of WBCs. In one embodiment, RBCs in the fluid sample typically also separate from the rare cells and the remaining other cells to one of the equilibrium positions $E_1$, $E_2$, $E_3$, $E_4$ in a square channel or one of the equilibrium positions $E_5$, $E_6$ in a rectangular channel. The RBCs typically also form a stream of RBCs. This is shown, for example, in FIGS. 8 and 9. The spacing between the individual streams of rare cells, WBCs, and RBCs is, for example, from 50 to 150 µm. In another embodiment, the spacing between the individual streams is from 80 to 120 µm. In still another embodiment, the spacing between the individual streams is about 100 µm.

A relation describing the magnitude of lift force ($F_z$) is:

$$F_z = \frac{\mu^2}{\rho} Re_p^2 f_c(Re_c, x_c)$$

where $Re_p$ is the cell Reynolds number, $Re_c$ is the channel Reynolds number, and $x_c$ is the position of the cell within the channel 12.

The phenomenon of Dean Flow may also play a role in the microfluidic device 10. Dean Flow tends to occur in the flow through a channel(s) 12 that is curved or non-linear. It is to be understood that a channel 12 that is curved is one that has one or more corners 24 or turns. Dean Flow tends to be a secondary flow due to centrifugal effects that affect equilibrium positions. Dean Flow tends to exhibit counter-rotating vortices wherein flow at a midline of a channel 12 is directed outward around a curve, while a flow at a top and bottom of a channel 12 are directed inward. This promotes separation of the cells. A small curvature is shown in FIG. 7A and a larger curvature is shown in FIG. 7B. The drag force due to Dean Flow tends to be correlated to a size of the cell and curvature of the channel(s) 12. In other words, the Dean vortices typically push the focused cells inward (toward the center of curvature) to new equilibrium positions. The magnitude of Dean vortices varies according to curvature, so cells migrate farther in sharper curves. The Dean Flow produces a drag force and can be expressed as $F_D$. The drag force typically affects an equilibrium position due to a balance with inertial force. Therefore, the equilibrium between inertial lift force and drag force from Dean Flow may be utilized for size-based sorting. Typically, fluid close to an inner wall of the channel 12 is drawn away from the center of curvature by centrifugal force, compensate flows form at the top and bottom of the channel 12, and accordingly two vortices appear at the top and bottom of the channel 12.

In the presence of inertial lift force that keeps a cell in a stationary position, an expression of drag force $F_D$ is typically $F_D \sim \rho U_m^2 a D_h^2 r^{-1}$, where $U_m$ is a maximum channel velocity, a is a diameter of the cell, $D_h$ is a hydraulic diameter, and r is a radius of a curve of the channel(s) 12. The lift forces tend to stabilize cells at positions located on the centerline of a channel cross section, while Dean Flow drags cells to circulate in the cross section. The new equilibrium positions are related to the ratio of $F_Z$ over $F_D$, which is a function of curvature ($\delta$) and cell size ($\alpha$). Therefore, a proper curvature could be used to separate various sized cells. A new equilibrium position can then be estimated from the ratio of $F_z$ to $F_D$ as follows:

$$\frac{F_z}{F_D} - \frac{1}{\delta}\left(\frac{a}{D_h}\right)^3 Re_c^n, \quad (n<0)$$

wherein $\delta$ is the curvature ratio, $$\delta = \frac{D_h}{2r}.$$

The rare cells of this disclosure may be isolated from bodily fluids in a microfluidic device 10 when flowed at a particular flow rate through channel(s) 12 having curvature. An inertial force can be described as a driving force that focuses the cells, while the drag force from Dean flow may be described as a force that migrates the cells from the center that leads to the size-based separation. In one embodiment wherein $F_D$ dominates, cells may not be focused due to the insufficiency of $F_z$, or cells having different sizes could be pushed to the same focusing position due to the strong migration force ($F_D$). In another embodiment wherein $F_z$ dominates, cells having different sizes may remain at the same equilibrium positions as that in a straight channel due to a lack of migration force. Selection of flow rate and curvature may be utilized to customize a ratio of $F_z$ to $F_D$ to maximize efficiency of cell separation.

It is contemplated that for cells flowing in outer loops (large radius of curvature) in microfluidic devices 10, the ratios for large and small cells are both greater than 1, which means the equilibrium tends to be dominated by lift force. This is similar to the situation of straight channel, where the cells tend to be focused closer to the center of channel regardless of the size of cells. For the cells flowing at inner loops (small radius of curvature) in microfluidic devices 10, the ratios for large and small cells are both close to 1, which means the equilibrium tends to be dominated by Dean Forces. In this scenario, the cells may be pushed to the inner wall by the strong Dean Force, in which both large and small cells are typically focused at the same position. Therefore, a position in between may be desirable, where the ratio for large cells is greater than the ratio for small cells, and the ratios are not too much greater than 1 nor too much smaller than 1. At such position, the cells can be well separated. In one embodiment, separation of the large cells (e.g. rare cells such as CTCs) occurs when the ratio is from 2 to 10. In another embodiment, separation of the large cells occurs when the ratio is from 5 to 8. In still another embodiment, separation of the large cells occurs when the ratio is from 6 to 7. Furthermore, and in one embodiment, separation of the small cells (e.g. white blood cells) occurs when the ration is from 1 to 5. In another embodiment, separation of the small cells occurs when the ratio is from 2 to 4. In yet another embodiment, separation of the small cells occurs when the ration is from 2 to 3.

Typically, a change in flow direction of the fluid sample (e.g. bodily fluid) in the microfluidic device 10 increases focusing of smaller cells, e.g. non-rare cells such as red or white blood cells. However, these smaller cells tend to be more difficult to focus due to the typical weakness of the lift force $F_z$. In the microfluidic device 10, Dean vortices may be generated at turns or curves (e.g. corners 24) in the channel(s) 12 such that cells are passively migrated along the vortices. This passive migration may transport the cells to their equilibrium positions. Once the cells are focused, a change in flow direction may not disperse a focused stream, which may result in the presence of turns or curves helping the focus of the cells without decreasing efficiency of the microfluidic device 10.

It is contemplated that the shape, length, number of curves, frequency of curves, and/or severity of curves may affect the efficiency of the microfluidic device 10. For example, in FIG. 8, the shape of the channels 12 in the microfluidic device 10 is shown to separate target rare cells (CTCs) from red blood cells and white blood cells.

Figure 2:
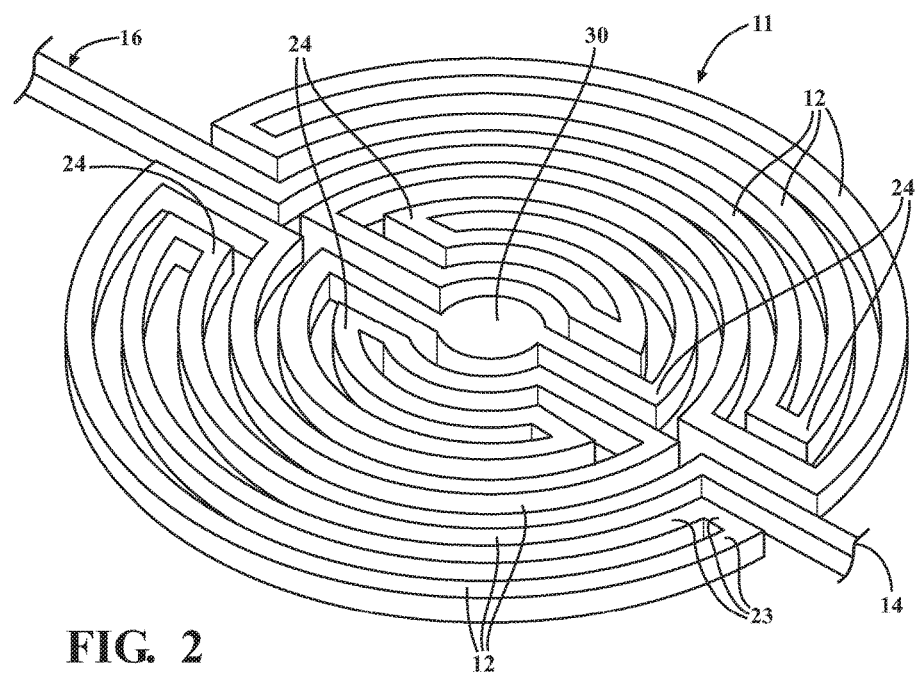
FIG. 2 is a perspective view of the channel(s) of another embodiment of the microfluidic device.
Figure 4K:
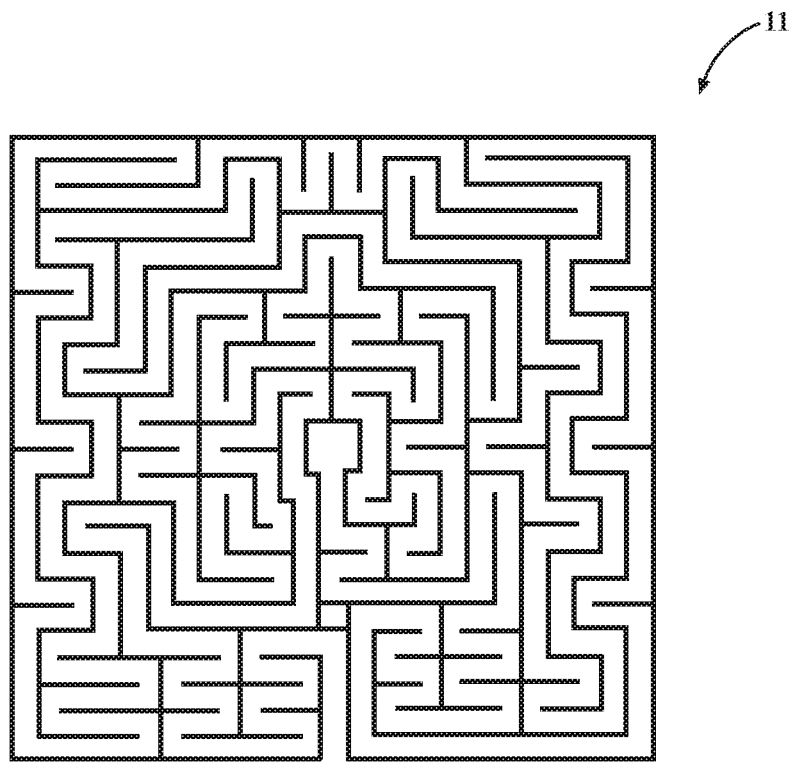

In one embodiment, the microfluidic device 10 includes numerous, e.g. a plurality of, corners 24, as shown in FIGS. 2 and 3 for example. It is believed that the change in flow direction can increase the focusing of smaller cells. Smaller cells (e.g. red blood cells (RBCs) and white blood cells (WBCs)) are more difficult to focus due, at least in part, to the weakness in the lift force $F_z$. It is further believed that small cells can be focused at sharp turns/corners 24 due to the strong Dean vortices at the corners 24. Accordingly, the small cells are passively migrated along the vortices, and this passive migration transports the cells to the equilibrium positions. For example, large cells are typically easily focused as they are already at the focusing position during passing through the corner 24. The smaller cells, on the other hand, are not focused yet at the corner 24. The focusing of the cell tends to be enhanced by the strong Dean vortex at the corner 24, which allows the cell to get closer to its focusing position after passing through the corner 24. The focusing of other cells may be enhanced by the other corner 24 in the opposite direction. In a related embodiment, the change of flow direction, i.e. clockwise or counterclockwise, may affect efficiency of the microfluidic device 10. For example, the equilibrium positions may always be close to an inner wall, and a change of direction may not disperse the focusing cells.

Cell focusing and separation may be improved in microfluidic devices 10 having many corners 24. However, cell focusing and separation can also occur in microfluidic devices having a small number of corners. In one embodiment, the microfluidic device 10 has two or more corners 24. In another embodiment, the microfluidic device 10 has from forty to fifty corners 24. In one specific embodiment, the microfluidic device 10 has about forty seven corners 24.

Figure 11A:
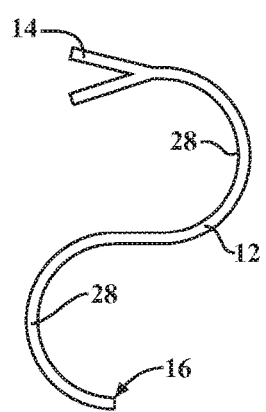
FIGS. 11A through 11C are top views of three embodiments of a channel of the microfluidic device.
Figure 11B:
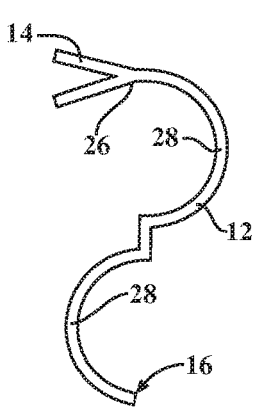
Figure 11C:
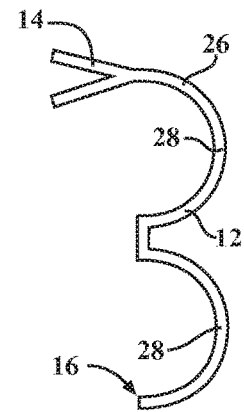

In one embodiment, each of the plurality of corners 24 includes at least a 90° change in direction of the flow of the fluid sample. For instance, as illustrated in FIGS. 11A through 11C, the microfluidic device 10 may include a channel structure that includes one or more first sections 26 proximate one or more inlets 14, one or more curved radial sections 28, one or more additional sections 26 forming two right angles, one or more additional curved radial sections 28, and one or more outlets 16. A connecting channel disposed intermediate to the curved radial sections 28 may be used to form one or more 90° turns between one or more semicircles, e.g. as shown.

In another embodiment, the microfluidic device 10 includes a channel structure that includes one or more first sections 26 proximate one or more inlets 14, one or more curved radical sections 28, one or more additional sections 26 forming one or more right angles in a U-Shape, one or more reverse curve radial section 28, and one or more outlet 16. A connecting channel may be used to form one or more 180° turns between one or more semicircles, e.g. as shown.

In other embodiments, the microfluidic device 10 include a planar labyrinth structure having one or more a curved channel(s) 12 and a plurality of (abrupt) turns that may fold laminar flow and shift elliptic points corresponding to centers of Dean Flow. The microfluidic device 10 may also include one or more than one circular chamber 30 disposed therein.

Figure 10:
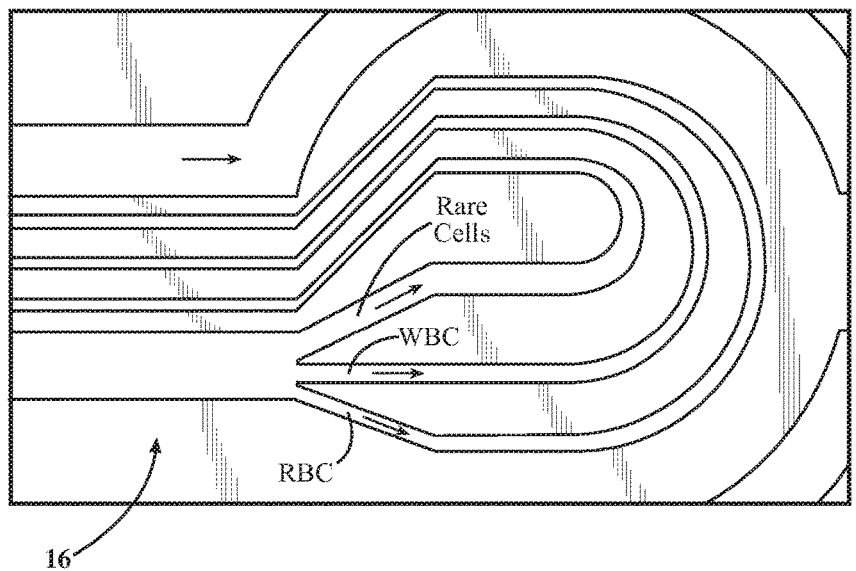
FIG. 10 is a schematic diagram showing how cells separate based on size in the outlet.

As shown in FIGS. 8-10, the outlet 16 typically comprises a number of flow paths for the separate streams of cells. As shown in FIG. 8, the outlet 16 typically comprises at least a first flow path for the stream of rare cells and a second flow path for the stream of WBCs. Other flow paths may be available for other cells in the fluid stream (e.g., RBCs and platelets). In FIG. 9D, for instance, the outlet 16 typically comprises six flow paths, where a first flow path is for the stream of rare cells, the second flow path is for the stream of WBCs, and the third flow path is for the stream of RBCs. In FIG. 10, the outlet 16 typically comprises three flow paths, where a first flow path is for the stream of rare cells, the second flow path is for the stream of WBCs, and the third flow path is for the stream of RBCs. Typically, the stream of cells (e.g. the stream of rare cells) are collected from the respective flow path, for example, for further analysis.

The microfluidic device 10 may also include or be coupled to one or more components such as reservoirs, filters, pumps, valves, actuators, pipes, tubes, electrodes, meters, computers, electronic monitoring devices, analytical devices, electrical potential and/or resistance monitoring devices, and the like. Those of skill in the art may select one or more of the components to couple to the microfluidic device 10.

In one embodiment, the microfluidic device 10 is coupled to a pre-depletion module. The pre-depletion module is not particularly limited and may be any known in the art. Typically, the pre-depletion module may be coupled to the microfluidic device 10 at an upstream and/or downstream end. For example, it is contemplated that blood or bodily fluids may be injected into the pre-depletion module and then flow into the microfluidic device 10. Alternatively, blood or bodily fluids may flow from the microfluidic device 10 into the pre-depletion module. Typically, the pre-depletion module separates additional red and or white blood cells from the target rare cells.

Additional Embodiments

In additional embodiments, the microfluidic device 10 includes the inlet for receiving the fluid sample and a means for separating the rare cells from the other cells in the fluid sample by causing the rare cells to move to an equilibrium position within a flow of the fluid sample when a ratio of inertial lift forces ($F_z$) and Dean flow ($F_D$) of the fluid sample is from 2 to 10, and an outlet for collecting the rare cells. In one non-limiting embodiment, the means for separating the rare cells from the other cells comprises at least one channel having a plurality of segments and a plurality of corners. In various other non-limiting embodiments, the means for separating may be any one or more channels, curves, segments, etc. described above or may include the labyrinth or maze described above.

Method for Forming the Microfluidic Device:

This disclosure also provides a method of forming the microfluidic device 10. The method typically includes the step of forming the microfluidic device 10 on the substrate. The microfluidic device 10 may be formed by any mechanism known in the art. For example, the microfluidic device 10 may be formed using pouring and molding techniques, e.g. as described in the Examples.

The method may also include the step of forming one or more channels 12 or chambers.

Method for Diagnosing Cancer:

This disclosure also provides a method for diagnosing a cancer or carcinoma in a subject. This method includes the step of introducing a sample of a bodily fluid to the microfluidic device 10 and determining whether any target rare cells are present. Rare cells obtained by the methods of the disclosure may be assayed for genetic information. In addition, the rare cells may be assayed for changes in genetic information over time as well as or in the alternative to enumeration, e.g. to monitor for the appearance of mutations that indicate a change in therapy is advisable.

Method for Lysing Rare Cells:

This disclosure further provides a method of lysing rare cells using the microfluidic device 10 of this disclosure. This method typically includes the step of introducing a sample of a bodily fluid to the microfluidic device 10 and subsequently introducing a lysing agent thereto. The lysing agent may be any known in the art.

One or more methods of this disclosure may also include the step of washing the rare cells at a high shear stress or volume to increase purity and reduce the number of weakly bound or non-specifically bound rare cells in the microfluidic device 10. One or more methods of this disclosure may also include the step of counting or quantifying a number of bound rare cells. The rare cells can be counted by any method known in the art, including optical, e.g. visual inspection, automated counting, microscopy based detection, FACS, and electrical detection, e.g. with the use of Coulter counters. Counting of the rare cells can be useful for diagnosing diseases, monitoring the progress of disease, and monitoring or determining the efficacy of a treatment. The number of rare cells may also be counted in non-medical applications, e.g. for determination of the amount, presence, or type of contaminants in environmental samples, pharmaceuticals, food, or cosmetics.

One or more of the methods of this disclosure may also include the step of measuring a desired characteristic of rare cells. For example, the method may include the step of measuring desired biological properties of rare cells such as mRNA expression, protein expression, and DNA quantification.

Various embodiments and examples of the microfluidic device and the method for detecting rare cells described above is a high throughput cell separation device for the enrichment of CTCs. By utilizing a balance between various hydrodynamic forces, the label-free device and method is typically usable for the separation of CTCs based, at least in part, on the size difference of CTCs and other cells in blood. In some examples, the microfluidic device includes a labyrinth channel structure, which allows cells to be efficiently separated with high throughput while ensuring desirable recovery and purity of CTCs. Even further, the microfluidic device having the labyrinth channel structure works well with whole blood samples, as well as samples of up to and including 1:5 dilution of whole blood.

To further illustrate examples of the present disclosure, the following Examples are given herein. It is to be understood that the Examples are provided for illustrative purposes and are not to be construed as limiting the scope of the present disclosure.

EXAMPLES

Cell Sample:

A prostate cancer cell line (PC3) is cultured and mixed with white blood cells extracted from blood. The concentration of PC3 is about 50,000 cells/mL. PC3 and white blood cells are stained with FITC (green) and DAPI (blue), respectively, for the observation using fluorescence microscopy.

Fabrication of the Mold:

A negative photoresist is utilized to form the mold for the microfluidic device by applying soft lithography. Using a spin-coater, a negative photoresist layer is deposited onto a silicon wafer with 2450 rpm rotating for about 1 minute. The wafer is then soft-baked for about 10 minutes at 65° C. and about 70 minutes at 95° C. A mask is aligned to the wafer and is exposed to UV light for about 20 seconds. Post-exposure-baking is applied for about 3 minutes at 65° C. and about 10 minutes at 95° C. Then, the wafer is developed by soaking in a developer for about 6 minutes and in IPA for about 1 minute to remove the inactivated photoresist. The wafer is hard baked for 3 to 5 minutes at 150 to 180° C. The height of the mold built on silicon wafer is 100 μm, and the width of the channel is 500 μm.

Figure 12:
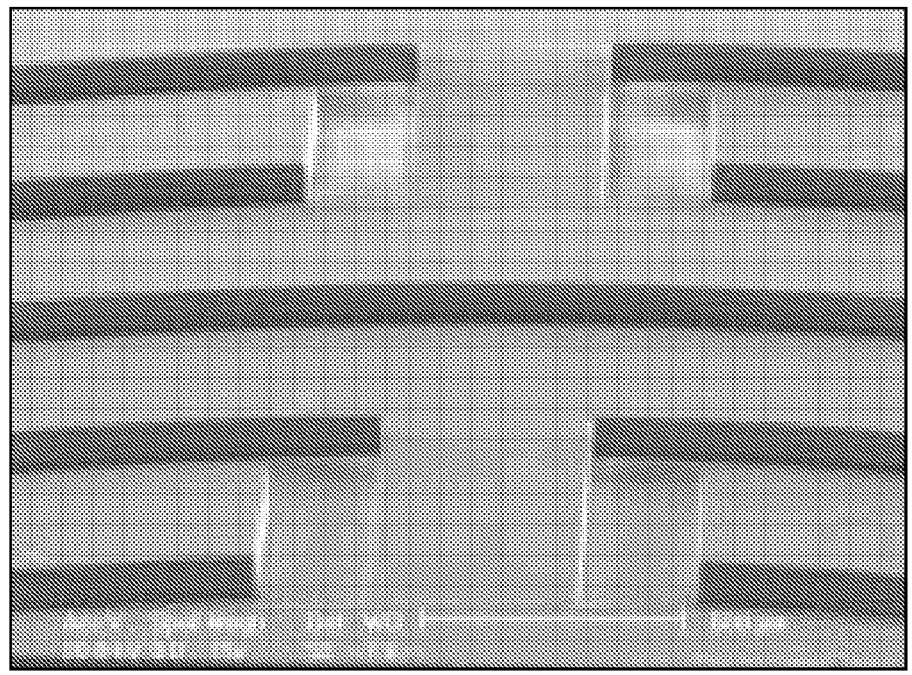
FIG. 12 is a scanning electron microscope (SEM) of a part of a microfluidic device.
Figure 13:
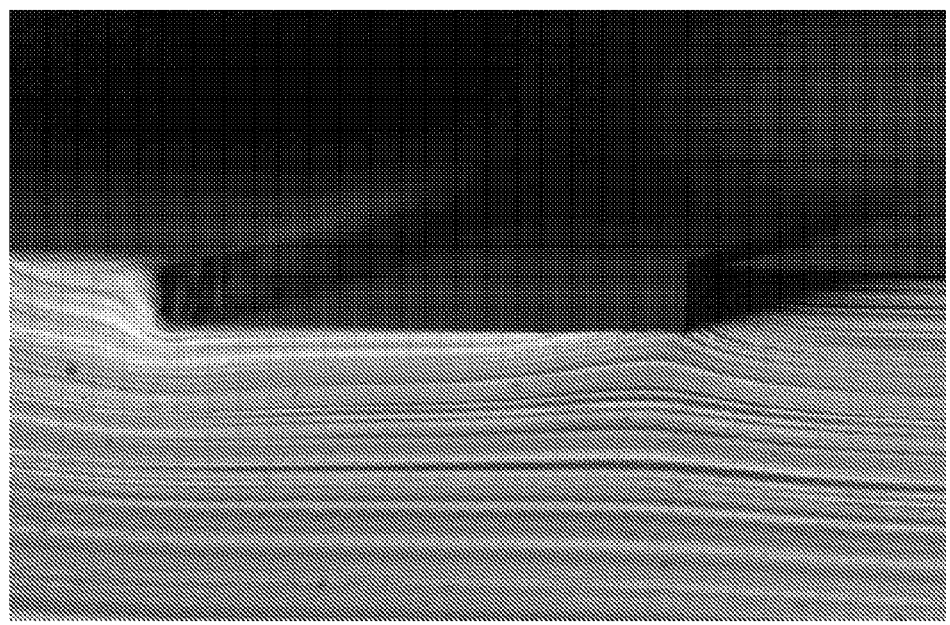
FIG. 13 is an SEM image of a cross-section of a microfluidic device.
Figure 14A:
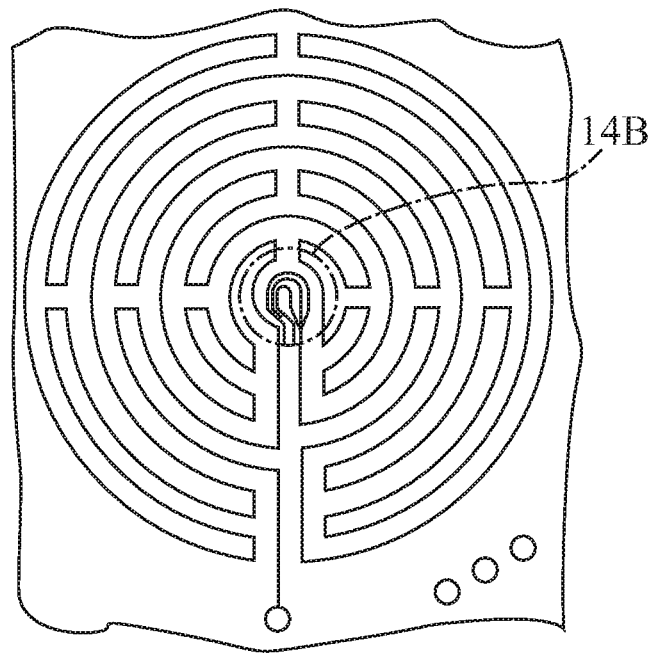
FIGS. 14A and 14B are schematic diagrams showing an example of a microfluidic device (FIG. 14A) having an outlet design (FIG. 14B) for the separation of cells to collect cells based on size.
Figure 14B:
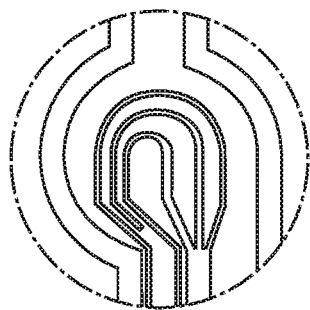
Figure 15A:
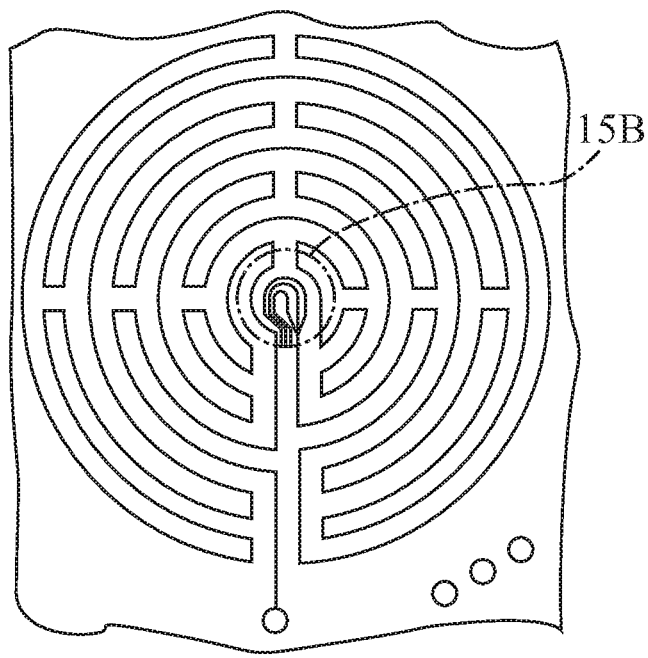
FIGS. 15A and 15B are schematic diagrams showing another example of microfluidic device (FIG. 15A) having an outlet design (FIG. 15B) for the separation of cells to collect cells based on size.
Figure 15B:
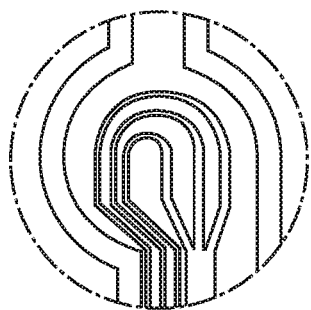
Figure 16A:
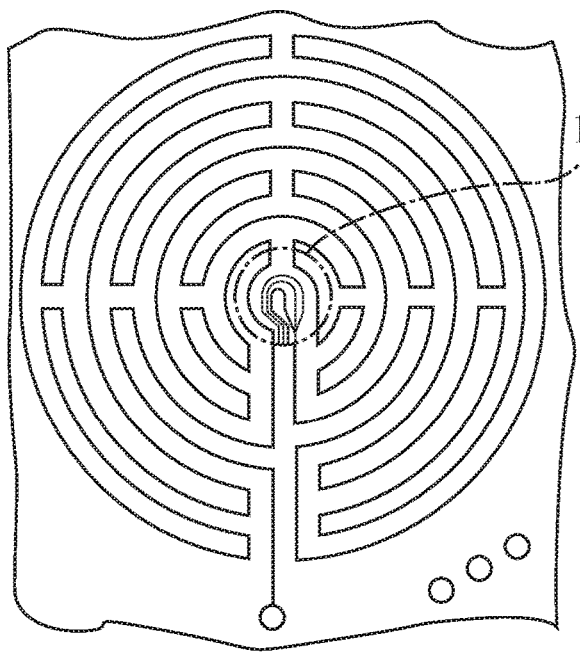
FIGS. 16A and 16B are schematic diagrams showing yet another example of microfluidic device (FIG. 16A) having an outlet design (FIG. 16B) for the separation of cells to collect cells based on size.
Figure 16B:
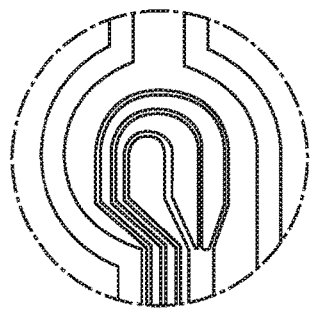
Figure 17A:
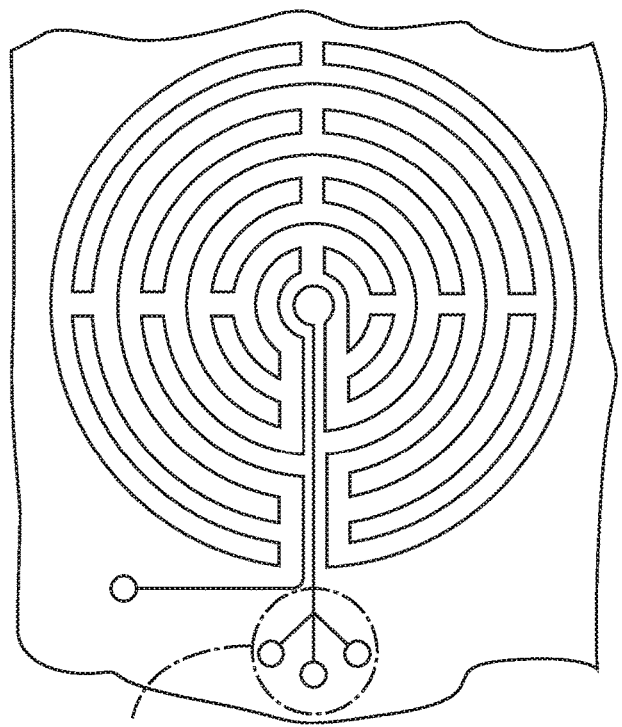
Figure 20A:
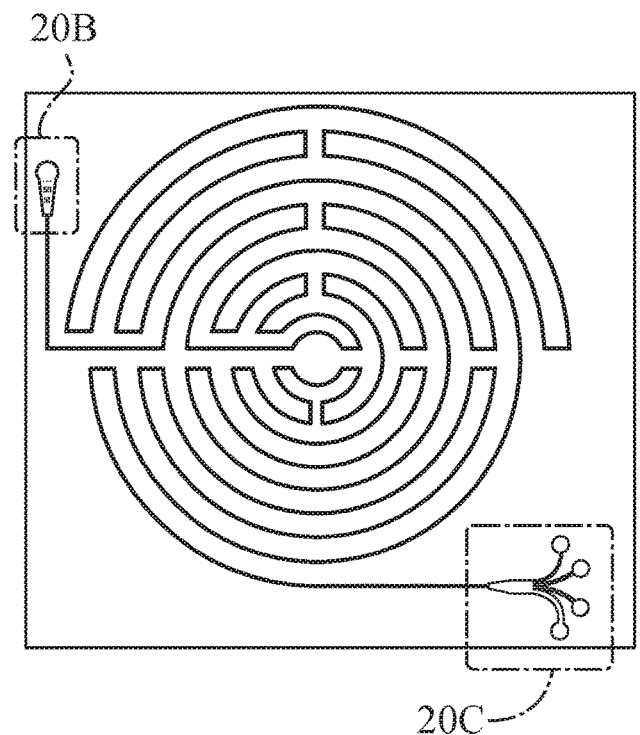
FIGS. 20A through 20C are schematic diagrams showing an example of an inlet design (FIG. 20A), a labyrinth channel design (FIG. 20B), and an outlet design (FIG. 20C).
Figure 20B:
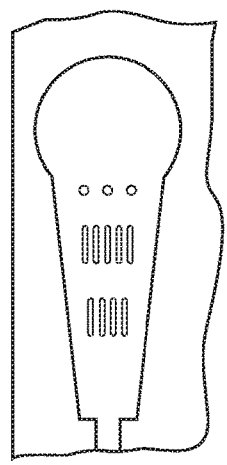
Figure 20C:
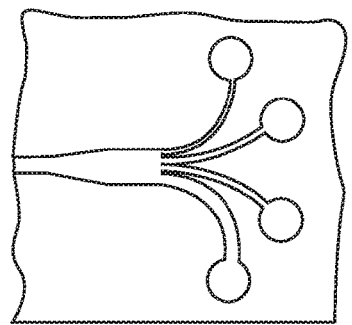
Figure 21:
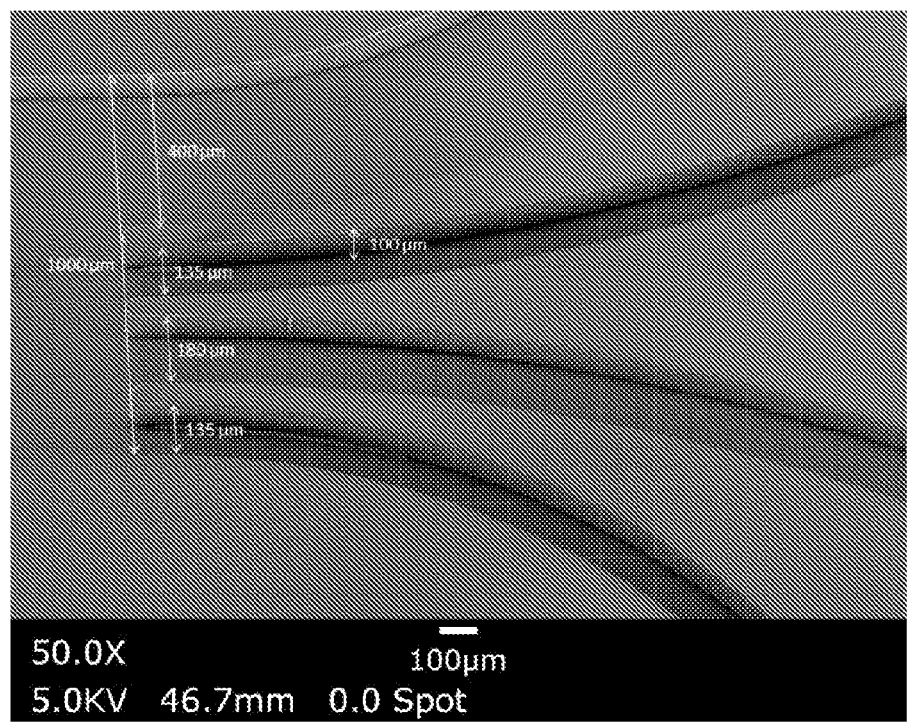
FIG. 21 is an SEM image of four outlet positions for separation of cells in a microfluidic device.

Fabrication of Microfluidic Device:

Samples of 30 mL Sylgard polymer commercially available from Dow Corning Corporation and 3 mL curing agent are well-mixed and poured onto various silicon molds. The mixtures are placed in a desiccator for about 2 hours to remove bubbles within the mixtures. The mixtures are then heated at 65° C. overnight to harden the polymer. The polymer is cut into various shapes (e.g. a rectangle for a labyrinth channel structure), and punched with a needle for tubing, thereby forming various microfluidic devices. The microfluidic devices are then bonded to standard sized glass slides via plasma surface activation of oxygen. The bonded microfluidic devices are tubed with 0.66 mm diameter tubes. Six variations of the microfluidic device are formed and are described in detail below. FIG. 12 is a scanning electron microscope (SEM) image of a part of one embodiment of the microfluidic device, and FIG. 13 is an SEM image of a cross section of a channel of one embodiment of the microfluidic device.

Experiment 1:

Each variation of the microfluidic device is pre-flowed with 1% Pluronic acid solution (diluted in 1×PBS) at 100 μL/min for 10 minutes to minimize cell clotting on channel walls. The devices are then flowed with cell samples at different flow rates and observed under microscopy. Images and movies under brightfield, FITC, and DAPI are captured.

Six variations of the microfluidic device are formed, see e.g. FIGS. 14-19. In an original design (FIGS. 14A and 14B), a channel is separated into three outlets at the center of the microfluidic device and outlet channels are inducted to an outer part of the device to facillitate the collection of products. Efficient separation is observed in an experiment with PC3/diluted blood sample. However, the outlet channels are blocked by the aggregation of clots soon after the experiment begins. This blocking at outlets hinders further collection of separated products and the application of this device.

In a second (FIGS. 15A and 15B) and third design (FIGS. 16A and 16B), various outlets are designed and tested. In these designs, the channel is first expanded before being separated into three at the center of labyrinth. Although the aggregation is reduced in several models, cells are not well separated in all of them. Observing the outlet design, the narrow duct of each of the three outlets may cause a pressure drop that dramatically lowers the flow rate at the outlet and thus result in the aggregation and poor separation.

In a fourth design (FIGS. 17A and 17B), and to avoid the narrow ducts, the channel is separated at the outer part of labyrinth, where it is much more spacious, into three equal-width outlet channels. A totally different separation is observed in these models: white blood cells go into top and bottom channels, while cancer cells go into the middle channel. However, the purity and recovery are not efficient enough, and also the separation results seem to be highly dependent on the sample. Therefore, a new experiment is created for a better understanding of the separation within the whole device.

From the previous experiments, it is observed that the separation relates to the position where the channel is separated into multi-outlet channels. In order to find the best position for placing the outlet, an additional design is formed while the sample is flowed.

In one additional design (FIGS. 18A and 18B), the microfluidic device is cut at the position found in previous experiments. A new outlet is also designed to reduce the aggregation and to perform better separation. Separation is observed and repeated in two experiments. High purity and recovery are also obtained from the collected product, see Table 1 below. In the fluorescent image taken at outlet channels, this device can still be optimized to reach a higher recovery.

TABLE 1

| Outlet | $1^{st}$ | $2^{nd}$ | $3^{rd}$ | $4^{th}$ |
| --- | --- | --- | --- | --- |
| WBC (blue) | 71.9% | 19.9% | 4.2% | 4.0% |
| PC3 (green) | 6.2% | 66.4% | 20.2% | 7.3% |
| WBC Removal | | | 71.9% | |
| PC3 Recovery | | | 93.8% | |

Subsequently, the outlet design is slightly modified to fit the separated flows observed in the previous experiments. The entire microfluidic device is also revised to complete the missing parts in the previous model, see FIG. 19. Both the purity and recovery are improved in this version, see Table 2 below. Fluorescent and high-speed videos are also captured to demonstrate the separation.

TABLE 2

| Outlet | $1^{st}$ | $2^{nd}$ | $3^{rd}$ | $4^{th}$ |
| --- | --- | --- | --- | --- |
| WBC (blue) | 75.2% | 20.1% | 3.8% | 1.0% |
| CTC (green) | 1.3% | 92.1% | 6.2% | 0.5% |
| WBC Removal | | | 75.2% | |
| PC3 Recovery | | | 98.8% | |

For size-based separation of CTCs, a high throughput, high purity, and high recovery microfluidic device is described above in the Examples. The microfluidic device of this disclosure allows for detection and separation of rare cells (CTCs) in 10 mL of sample within 5 minutes. In the experiments, cancer cells are concentrated and mostly conserved (75% white blood cell removal and 99% recovery).

Experiment 2:

Additional experiments with a buffer sample were performed for characterizing and optimizing a labyrinth channel structure. A breast cancer cell line with green fluorescent protein (MCF-7/GFP) is cultured and mixed with white blood cells (stained with DAPI) into a buffer solution (PBS). For observation using fluorescence microscopy, the number of MCF-7/GFP spiked is around 50,000 cells/mL. The labyrinth channel structure is pre-flowed with 1% Pluronic acid solution (diluted in 1×PBS) at 100 μL/min for 10 minutes to prevent cell clotting on channel walls. The labyrinth channel structure is flowed with buffer or blood sample (high number of cells) at different flow rates and is observed under the microscope. For observation using fluorescence microscopy, images and movies under brightfield and fluorescence (FITC and DAPI) are captured. Waste from each flow path of the outlet of the microfluidic device is collected for counting the cells and calculating recovery and purity.

Experiment 3:

The same procedure as Experiment 2 is applied to collect the waste from main outlet (2nd outlet). The suspension cells in the waste are then centrifuged onto glass slides through cytospin. The standard process of cell staining is applied on the slides, where all cell nuclei are stained with DAPI (blue), WBCs are stained with CD45 (green), and cancer cells are stained with CK (red). The slides are scanned through fluorescent microscopy and manually counted. Only cells (DAPI+) with CK positive (CK+) are recognized as cancer cells, while cells with CD45 positive (CD45+) or double positive (CK+, CD45+) are classified as WBCs.

Advanced Design with Four Outlets:

New flow paths for the outlet of the device are designed to reduce the aggregation and to perform better separation, see, e.g. FIGS. 20A through 20C and FIG. 21. A filter (shown in FIG. 20A) is placed at the inlet to reduce the debris that may go into labyrinth channel structure (shown in FIG. 20B) and block the channel at the outlet (shown in FIG. 20C and FIG. 21). The width of each branch channel is 400, 135, 180, 135 μm, respectively.

Figure 22:
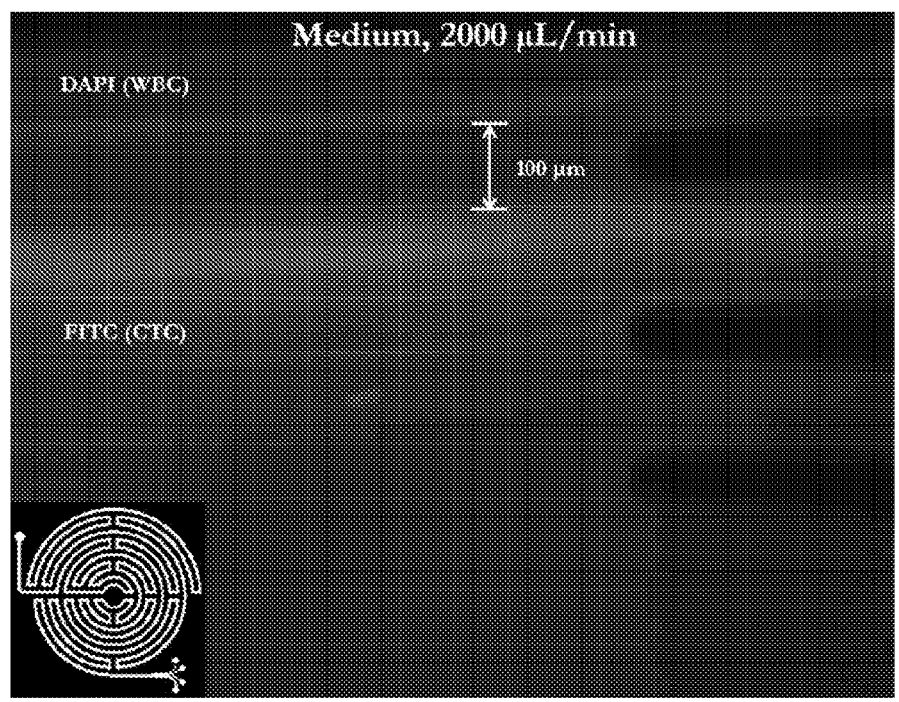
FIG. 22 is a fluorescence microscope image of focusing and separation of CTCs and white blood cells (WBCs).
Figure 23:
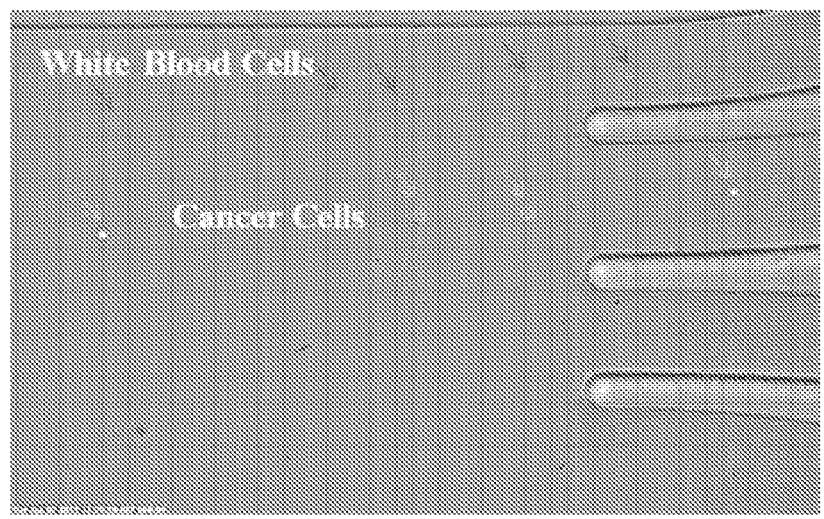
FIG. 23 is an image of focusing and separation of CTCs and WBCs utilizing a high speed camera.

Separation of Cancer Cells and White Blood Cells:

About 95.92% recovery of MCF-7 cells and 87.81% WBC removal from diluted blood sample (20-fold dilution) is observed in the product from the second flow path of the outlet. The separation is repeated and recorded with fluorescence microscopy and high speed camera at the cellular level, as shown in FIGS. 22 and 23.

Experiment 4:

In order to predict the performance of the microfluidic device including the labyrinth channel structure for a real patient sample, a low number of cancer cells (100 cells/mL) are spiked into buffer or blood (from healthy donors) to mimic the extremely low occurrence of CTCs in patients. Separation of cancer cells is similar to previous experiments resulting in a high number of cancer cells isolated. In the buffer sample, an average of 95% cancer cells is found in the effluent from the second outlet. Recovery of spiked cells increased from 49% to 78% after changing the connection tubing from large tubes (ID: 0.02 in) to small tubes (ID: 0.01 in). In the blood sample, similar results are observed: 95% of cancer cells are focused to the second outlet and 66% of spiked cells are recovered (see Table 3).

TABLE 3

| Sample | Spiked Cells | $1^{st}$ Outlet | $2^{nd}$ Outlet | $3^{rd}$ Outlet | $4^{th}$ Outlet | Recovery$^1$ | Recovery$^2$ |
|---|---|---|---|---|---|---|---|
| Buffer | 100 | 3.33 | 77.67 | 1.67 | 0 | 78% | 94% |
| Blood | 100.5 | 1.75 | 66.25 | 2.00 | 0.00 | 66% | 95% |

The results in Table 3 are calculated from the average of experiments on four individual devices. Recovery is based on the spiked cells sent into labyrinth. Recovery is calculated from the mass balance of each outlet.

Depletion of Unwanted White Blood Cells for Better Purity:

High efficiency is observed in the microfluidic device such that 95% of spiked cancer cells are recovered and 80% of WBCs are removed. However, the number of remaining WBCs in the collected products from labyrinth is still much higher than the number of cancer cells. In general, several million WBCs are found in 1 mL of whole blood, while only tens of CTCs may appear in each mL of blood. The amount of WBCs can still be around one million after processing by microfluidic device.

Capture of White Blood Cells with Depletion Device:

CD45 (lymphocyte common antigen) is a receptor-linked protein tyrosine phosphatase that is expressed on all leukocytes, and which can be applied on the WBC depletion device using immune-based capture. A PDMS CTC-Chip with CD45 functionalization is selected as the depletion device due to its high surface contact area and high efficiency in capturing targeted cells. The depletion device is tested with different antibody concentrations, flow rates, and blood dilution ratios to determine the best condition for WBC capture. High capture efficiency of WBCs is demonstrated with no cancer cell trapped within the depletion device. However, hundreds of WBCs per mL are still found in the final product. It is believed that it may be useful to functionalize the depletion device with more than one kind of antibody. Multiple antibodies (CD45, CD15, and CD11b) can be used for better depletion.

Red Blood Cell Removal:

In some evaluations, RBCs are not focused or removed by the microfluidic device and a significant amount of RBCs cannot be neglected in further analysis of the collected product. In other evaluations, the microfluidic device is capable of reducing the number of RBCs from 5 billion per mL of whole blood by approximately 75%. Although RBCs are much smaller in size (5-6 μm) in comparison to cancer cells (18-20 μm) and un-nucleated, the large number of remaining RBCs may still obstruct the delicate process of single cell analysis. RBC lysis is a commonly used technique to remove the RBCs. Nevertheless, other cells, including targeted cancer cells, can also be lysed during the process and the efficiency of the device would be decreased.

Straight channel devices with various aspect ratios are fabricated and tested with different flow rates and blood dilution ratios in order to observe the flow patterns of blood cells. It is hypothesized that larger cells are typically pushed away from the main stream, i.e. WBCs and CTCs, and be closer to the side walls. The goal of the straight channel device is to use fluid dynamics properties to collect the cancer cells and WBCs from outlets at side walls while RBCs can be kept in the main channel. Cancer cells and WBCs can be separated from RBCs and typically then be further separated by the microfluidic device including the labyrinth channel structure and the depletion device. However, the results from straight channel experiments do not demonstrate a good separation of cells. Larger cells are pushed to the side of the main stream but not close enough to the walls to be removed.

Several temporary solutions for reducing the number of RBCs are examined. Since the microfluidic device including the labyrinth channel structure can reduce the RBCs to a quarter of the original amount in blood, it is believed that a second or third labyrinth channel structure may reduce the number of RBCs to one sixteenth or one sixty-fourth. A double labyrinth channel structure is tested and the overall separation of cancer cells is reduced from 95% to 80% while WBC removal rate is increased from 80% to over 90%. The efficiency reduction is acceptable, while the increase in RBC and WBC removal can benefit the final purity of the collected product. Another approach to remove RBCs is to use Dextran to create a density gradient in the blood sample and physically remove RBCs. The density-based separation is a physical process and can minimize the effect on cancer cells.

Blood Dilution Ratio:

The microfluidic device is tested in various blood dilution ratios ranging from 1:5 to 1:50 (blood:buffer solution). No significant difference is found in the device operation under these conditions. However, the performance of microfluidic device is not fully functional until 30 seconds after starting the flow due to the time required to establish steady flow and focus particles. This implies that CTCs and CCSCs processed in the first 30 seconds can be lost. While higher dilution ratio, e.g. 1:50, may lead to fewer cells lost in the first 30 second since less cells are processed over the period, it also results in an overall longer processing time due to the larger volume of diluted sample. One solution to deal with this issue is to separately collect the effluent before and after 30 seconds of operation. In this case, a portion of sample is discarded, but low dilution ratio can be adopted while the cancer cell recovery can still be satisfactory.

Time Control:

The preparation of each device or process may require planning to reach the best performance for each step and to minimize idle time. For example, it may require two and a half hours to prepare the depletion device. The device may have the best capturing capabilities when freshly prepared. The density separation of RBCs using Dextran is stood stationary for 45 minutes. In one embodiment, the microfluidic device with the labyrinth channel structure is flowed with Pluronic solution for 10 minutes and incubated for another 10 minutes prior to use. These steps can be well-planned and executed in sequence that ensures correct timing.

Experiment 5:

Peripheral blood is collected from 20 breast cancer patients and is analyzed. RBCs are first removed from patient blood using either density separation (Dextran) or the aforementioned microfluidic approach. The mixture of CTCs and WBCs is diluted with PBS to an optimized dilution ratio and is processed through the microfluidic device at 2 mL/min. The collected product from the microfluidic device is processed through depletion device at 1.5 mL/hr. The separated CTCs are spread onto glass slides using Cytospin (15000 rpm, 10 mins) and stained for different markers (Cytokeratin for cancer cells, CD45 for leukocyte, and DAPI for cell nucleus). The markers are conjugated to secondary fluorescent dyes and automatically imaged using fluorescence microscopy. The criteria for a positive CTC are CK+/DAPI+/CD45−. To set the threshold for number of CTCs for diseased versus healthy individuals, blood collected from 10 healthy individuals is through the microfluidic device and CTCs are identified using the same criteria described above. A threshold for CTCs is established by comparing CTCs recovered from disease and healthy individuals.

Furthermore, to confirm the origin of the cells detected using the microfluidic device, breast specific markers are used. Isolated cells are immunostained with HER2 and are examined for HER2 gene expression using RT-PCR.

Figure 24:
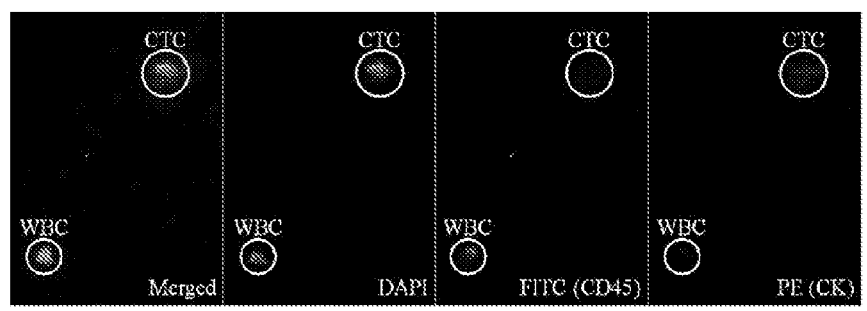
FIG. 24 is a fluorescence microscope image showing the isolation of CTCs from a pancreatic patent sample.

CTCs are discovered in several preliminary tests on cancer patients. FIG. 24 shows the fluorescence image of the collected product, where a CTC (CK+, DAPI+, CD45−) and WBC (CK−, DAPI+, CD45+) are both present. CTCs are larger in size with DAPI+m CK+, and CD45−. The WBCs are DAPI+ and CD45+.

Characterization of Circulating Cancer Stem Cells in Breast Cancer Patients:

Cancer stem cells may be the first step in EMT where cells are transited from epithelial to mesenchymal phenotype, which can lead to metastasis.

Stem cell biology generally provides new insights into cancer biology. In particular, similarities between stem cell biology and cancer biology includes (i) in the mechanisms that regulate self-renewal of normal stem cells and cancer cells, (ii) the possibility that tumor cells might arise from normal stem cells, (iii) the notion that tumors may contain stem like cells. The rare cells may drive the formation and growth of tumors. Furthermore, tumors may arise from a small subpopulation of tumor cells known as the cancer stem cells or tumor initiating cells. Using cells derived from primary breast tumors and metastatic pleural effusions that are grown in non-obese diabetic/severe combined immunodeficient (NOD/SCID) immunocompromised mice, one can distinguish a tumorigenic cell population characterized by the expression of the surface receptor CD44 (CD44+) and the absence of the cell-surface markers CD24 (CD24−) and a panel of non-epithelial lineage markers (lin), alone or in conjunction with the expression of the epithelial specific antigen (ESA). Transplantation of a small number of these cells, as few as 200 cells, formed in tumors recapitulated the phenotypic heterogeneity of the original tumors in NOD/SCID mice. However, transplantation of up to million CD44+/CD24+/lin are unable to form palpable tumors in the same mouse model. Accordingly, identification and further characterization of CSCs in solid tumors has contributed to the enunciation of the CSCs hypothesis, which poses that most, if not all, tumors arise from the transformation of either adult stem cells or early progenitors cells that lead to the different molecular and clinical phenotypes observed. In the case of breast tumors, stem cells generate a cellular progeny with incomplete differentiation phenotypes that correlate with the distinct molecular subtypes. It is believed that the accumulation of transforming mutations in these cells, different in their phenotypic and functional properties, could explain the heterogeneity of breast cancers.

Since the isolation technique developed in Specific Aim 1 is antibody independent, it is hypothesized that the circulating tumor cells isolated using microfluidic device with the labyrinth channel structure includes or are cancer stem cells (CSCs). To identify these cells in patient samples, the following strategies are implemented.

To identify the breast CSCs capable of invasion and metastasis, multiple strategies involving various biomarkers and/or combination of markers may be employed. Generally, using cell surface molecules, putative stem cells may be in an isolated form of solid tumor tissues of the breast. The most commonly used criteria for breast cancer to define a stem-like cell is CD44+/CD24−. A progenitor marker (CD133) has been used, and it has emerged as a key marker for enriching cancer stem cells in many cancers. Aldehyde dehydrogenase 1 (ALDH1) may be used as another marker identifying putative breast cancer stem cells. Both normal and cancerous human mammary epithelial cells with increased ALDH1 activity have phenotypic and functional characteristics of stem cells. Moreover, breast cancer cells with high ALDH activity and the CD44+/CD24− phenotype generally has enhanced tumorigenic capacity compared to cells displaying high ALDH but lacking the CD44+/CD24− expression pattern. Additionally, in breast carcinomas, the expression of ALDH1 detected by immunostaining is correlated with poor prognosis. Accordingly, a combination of markers to identify CSCs from peripheral blood may be used.

As a first step, the developed system may be tested and optimized for detecting CSCs using established cell lines. CSC populations exist within breast cancer cell lines. Cell lines with different percentage of CSC presence are selected, including 100% population ALDEFLUOR positive (SK-BR-3, HCC38), greater than 5% of population being positive (SUM149, SUM159, SK-BR7), and less than 5% of population positive (MCF-7, HCC 1954, ZR-75-1, SUM 225), to ensure the sensitivity is enough to isolate CCSCs from billions of cells in patient blood. The blood samples drawn from breast cancer patients are tested after the system is characterized. Blood samples are processed as the standard protocol of the microfluidic device including the labyrinth channel structure except for which antibodies are used in the staining process. In the staining process, a combination of biomarkers, including CD44, CD133, ALDH1, CD24, and CD45, is used to distinguish the CCSCs from CTCs and WBCs. For CCSCs, the cells that are positive for at least two of the stem cell markers, CD133, CD44, and ALDH1 and negative for both CD24 and CD45. Cell lines relevant to breast cancer are first tested in order to characterize and optimize the labyrinth channel structure before testing patient blood samples. In the test of patient samples, the enriched CCSCs from labyrinth channel structure will also be processed through Fluidigm single cell mRNA Sequencing to sequence the mRNA. The Fluidigm technology can analyze 96 single cells for 96 different genes simultaneously to provide the information regarding stem cell pathways (e.g. Wnt and Notch), new transcripts and mutation. Examination of known and potential stem cell biomarkers can also be performed to identify the expression of them on CCSCs. Specifically, a number of genes can play a role in stem cell biology include NFYA, NOTCH2, PCNX, RBM15, ST3GAL3, and TPRXL, and are investigated. Other genes encode proteins with a putative or uncharacterized role in stem cell function, such as ARID1B, RAD51L1, and the chemokine receptor CXCR1/IL-8RA is also examined. Furthermore, to confirm the results obtained using DNA microarrays, in some patients, RNA is extracted from the cell lysate for qRT-PCR analysis. In addition to the candidate genes emerged from genomic DNA, five discriminator genes that are generally over expressed in ALDEFLUOR-positive populations are also used. The five specific genes are CXCR1/IL-8RA, FBXO21, NFYA, NOTCH2, and RAD51L1. Again, as a control, the genomic DNA and/or RNA extracted from the capture experiments performed are used on samples extracted from healthy individuals.

Accordingly, detection of the presence of CSCs in the peripheral blood of breast cancer patients is desired. Furthermore, a correlation to disease stage is determined and not only validate/confirm the stem specific candidate genes, but also may elucidate specific unique signatures that can be used for designing therapeutic targets.

Monitoring the Cancer Stem Cell Therapies Efficacy in Breast Cancer Patients:

CSC isolation is used not only for the characterization of their biological properties, but also for the development and monitoring of cancer stem cell therapies. The presence of CSCs is proposed as a factor in the development of therapeutic resistance and relapse in breast cancer. The enrichment of CD44+/CD24− cells after administration of chemotherapy inmplies that CSCs are resistant to drugs and can repopulate the tumor due to their self-renewal potential. The elimination of the CSC population would prevent the remaining cells from promoting new tumor growth. Therefore, the most efficient treatment strategy would be the combination of CSC population elimination and other current therapies such as chemotherapy.

An approach in CSC treatment is to target CSC surface markers such as CD44 or ALDH1 with specific antibodies. Also, targeting the Notch pathway, which is a signaling pathway for CSC self-renewal, could lead to the elimination of CSCs. It is believed that the genetic suppression of antiapoptotic proteins such as FLICE-Like Inhibitory Protein (c-FLIP) could reduce the CTC resistance to apoptosis.

In the clinical trial of cancer stem cell therapies, the monitoring of CTCs and the characterization of CCSCs can be indicators of the clinical efficacy. The developed system may be used to quantify CTCs from patients before therapy, before each new cycle, and at the end of therapy. To characterize CCSCs from patients after therapy, and the protocol and criteria is applied to track the response of CCSCs to the therapies.

Determining Viability of CTCs After the Labyrinth:

High shear in the labyrinth channel structure can affect cell viability. Hence the effect of the labyrinth channel structure on not only viability but also on proliferation is examined. Cell viability is assessed using the MTT ((3-(4, 5-Dimethylthiazol-2-yl)-2,5-diphenyltetrazolium bromide) colorimetric assay.

In principle, MTT is taken up into cells by endocytosis or a protein-facilitated mechanism and is reduced by mitochondrial enzymes to yield a purple formazan product which is largely impermeable to cell membranes, resulting in its accumulation in living cells. Solubilization of the cells results in the liberation of the purple product, which can be detected using a colorimetric measurement at 500-600 nm. The ability of cells to reduce MTT provides an indication of the mitochondrial integrity and activity, which, in turn, may be interpreted as a measure of cell viability. Since measurements for this assay are taken at several time points, normalization of cell number at each time points over the initial cell can give a measurement for cell proliferation.

After recovery from the labyrinth, Panc-1 cells are cultured for 7 days and compared with an appropriate control (unprocessed cells) to study cell viability. Cells started proliferating just 24 hours after being incubated, increasing their population by 50% within just three days. Cells seem to pass through the exponential growth phase, followed by a stationary phase during day 5. In this phase, cells start to compete for limiting essential factors that enhances cell growth in any cell, such as media nutrients and space. Due to the lack of spatial availability, cells typically enter in a death phase, at which point it can be presumed that the culture well includes the maximum number of cells. These trends are observed for the control as well as processed cells. This shows that the shear stress that cells experience in the labyrinth channel structure does not significantly affect their viability or their proliferation rates. Higher cell growth is observed in the labyrinth channel structure.

Experiment 6:

Techniques such as immunocytochemistry are used to analyze protein expression. In addition, extraction of RNA from CTCs enables protein expression analysis at a cell transcript level. This step may enable one to perform RT-PCR, giving more insight into the high heterogeneity observed within CTC population. Since the microfluidic device allows the collection of live CTCs, culturing these cells is another approach for performing both genomic and functional assays. This may help profile CTCs to achieve better understanding of the pharmacodynamics of pancreatic cancer.

Patient Sample Processing without Pre-Treatment:

The labyrinth channel structure is pre-flowed with 1% Pluronic acid solution (diluted in 1×PBS) at 100 μL/min for 10 minutes to prevent cell clotting on channel walls. The blood sample is then processed through the device at a flow rate of 2 mL/min. Flow stabilization takes about 1 minute, so recollection of the second outlet starts after 1 minute. Second outlet product is processed using Thermo Scientific™ Cytospin 4 Cytocentrifuge. A 300 μL of sample is inserted into each cytospin funnel and cytocentrifuged at a speed of 800 rpm for 10 minutes. Samples are fixed on the cytoslides using 4% PFA and cytocentrifuged at the same conditions described above. Cytoslides are stored at 4° C. for further staining.

RNA Extraction:

Once samples are collected from the device, they are centrifuged for supernatant removal at 1000 rpm for 4 minutes. This is followed by addition of 150 μL of RNA extraction buffer, gently mixing the sample. Samples are incubated for 30 minutes at 42° C. The samples are stored at −80° C. for RT-PCR analysis.

Immunostaining Protocol of Cytoslides:

Samples are permeabilized by applying 0.05% PBST solution for 15 minutes. Slides are then blocked using 20% donkey serum for 30 min at room temperature (RT). A cocktail of primary antibodies is added and left in a humidified chamber overnight. Next day, cytoslides are washed thrice with 0.05% PBST for 5 minutes. Samples are incubated in dark with secondary antibodies for 45 minutes at RT. Finally, samples are washed thrice with 0.05% PBST for 5 minutes and mounted with Prolong Gold with DAPI.

Culturing Patient Samples for CTC Expansion:

Recollected sample from second flow path of the outlet is plated in a Petri dish flask (size according to the volume received from blood donor) and cultured at 37° C. incubation chamber. After 24 hours of incubation to enhance cell adhesion to the flask, sample buffer is aspirated and then replaced with conditioning media. This media is changed every 48 hours to ensure cell expansion.

Immunocytochemistry Analysis of CTCs:

The study of immunocytochemistry expression on CTCs allows the quantification of these cells along with the exploration of the potential of CTCs as a surrogate for tissue biopsies. This assay enables use of pancreatic cancer related cell markers not only to identify but to quantify different subpopulations of CTCs found on each patient sample. More specifically, the expression level variance among subpopulations related to epithelial, mesenchymal or stem-like cell markers is desired.

Preliminary results from three patient samples, shown in Table 4, are obtained by recovering the product of the second outlet from the labyrinth. These samples are then processed through the Cytocentrifuge, where CTCs are attached onto the glass cytoslides for staining purposes.

For quantification purposes, the standard definition of CTC is followed: cells that express the nuclear stain DAPI, stain positive for cytokeratin and negative for CD45. Cytokeratins are an intermediate filament found only on epithelial cells, while CD45 is a leukocyte common antigen found only on WBCs. Following this standard, proper quantification of CTCs is compared with the CA stage of each patient. Table 4 shows that the number of CTCs per mL correlates to the cancer stage on each patient.

TABLE 4

| Patient Code | CTCs/mL | CA Stage |
|---|---|---|
| F | 13.2 | III or IV (locally advanced) |
| G | 2.6 | III |
| H | 0 | Early stage |

This data shows that the labyrinth channel structure is capable of processing blood from pancreatic cancer patients for CTC screening. Accordingly, it is possible that different subpopulations could be more mesenchymal or stem-like than expected. This will cause a decrease on the expression of epithelial markers, such as cytokeratins, and may not be considered as CTCs according to the standard definition. However, it is possible that there can be overexpression of stem cell and epithelial-mesenchymal transition markers in CTCs.

Figure 25:
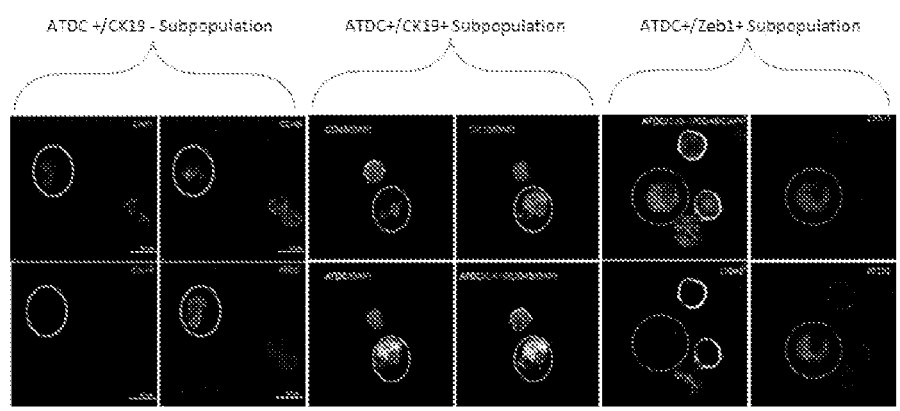
FIG. 25 are images of immunofluorescence staining of three subpopulations found in a patient sample.

Using the labyrinth different subpopulations of CTCs on a patient is discovered. Different cell markers are used for this study: Ck19, ATDC, and Zeb1. CD45 is used as a negative control, since it is a membrane marker solely expressed on WBCs. Ck19 is an epithelial marker commonly expressed on pancreatic cancer cells. ATDC has been identified as a protein highly expressed in the majority of human pancreatic adenocarcinomas and pancreatic cancer precursor lesions. Furthermore, ATDC in pancreatic cancer cells as been expressed which promotes cellular proliferation and enhanced tumor growth and metastasis. Lastly, ZEB1 is a transcriptional repressor that is identified as an inducer of epithelial-mesenchymal transition (EMT), which is demonstrated to contribute to the malignant phenotype of pancreatic cancer cells. Confocal imaging of the three subpopulations observed on the patient is shown in FIG. 25. Co-localization of two of these markers (excluding the negative control marker CD45), is a different subpopulation having different epithelial and mesenchymal expression levels. This indicates a strong correlation to the EMT process. Molecular analysis on these subpopulations is still ongoing, as well as the quantification process in Table 5.

TABLE 5

|  | CD45+/ATDC+ | CK19−/ATDC+ | CK-19+/ATDC+/CD45+ | CK19+/ATDC+ |
|---|---|---|---|---|
| Total Cells per 300 μL of whole blood | 2 | 1 | 121 | 37 |

Cell Expansion Studies on CTCs:

Although tumors can be formed in animals by cells from the peripheral blood of patients, long-term culture of isolated human CTCs has rarely been reported. Since the labyrinth channel structure allows isolation of CTCs with minimal effect on cell viability, cell expansion of CTCs obtained from pancreatic cancer patients can be facilitated. Fibroblasts cells are of particular interest for potential study in co-culture since they are associated with cancer cells at all stages of cancer progression, and their structural and functional contributions to this process still an area of active research. This approach is accomplished with another patient sample (Table 6), where CTCs are sustained in culture for 7 days using cancer associated fibroblast (CAF) growing media, also known as conditioning media.

TABLE 6

| CK-19 | EpCAM | Bmi1 |
|---|---|---|
| Zeb1 | Her2 | ATDC |
| Nestin | CK-8 | Shh |
| Twist | CK-18 | Slug |
| c-Met | TGF-β | Snail1 |
| E-cadherin | Vimentin | Fsp1 |
| CXCR4 | CD24 | PTEN |
| CD133 | CD45 | ESA |
| B-catenin | ALDH1 | c-Myc |
| Gli1 | Wnt | PDX1 |

Figure 26:
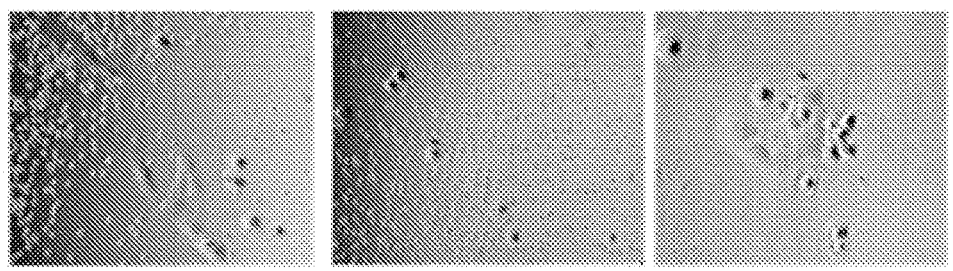
FIG. 26 are brightfield images of CTCs cultured for seven days.

In order to expand CTCs obtained from patient samples, the product of the second outlet from the microfluidic device is recollected and placed in cell culture chambers and incubated overnight at 37° C. Conditioning media is then added 24 hours after initial placement, allowing proper time for cell attachment onto the chamber walls. Although some RBCs and WBCs contamination from the second outlet is observed (see FIG. 26), their inability to grow or attach under these cell culture conditions ensures gradual removal of most contaminating cells. Cell viability is enhanced by conditioning media replacement every 48 hours, until day 7. CTCs are then fixed with 4% PFA for immunocytochemistry assay.

Figure 27:
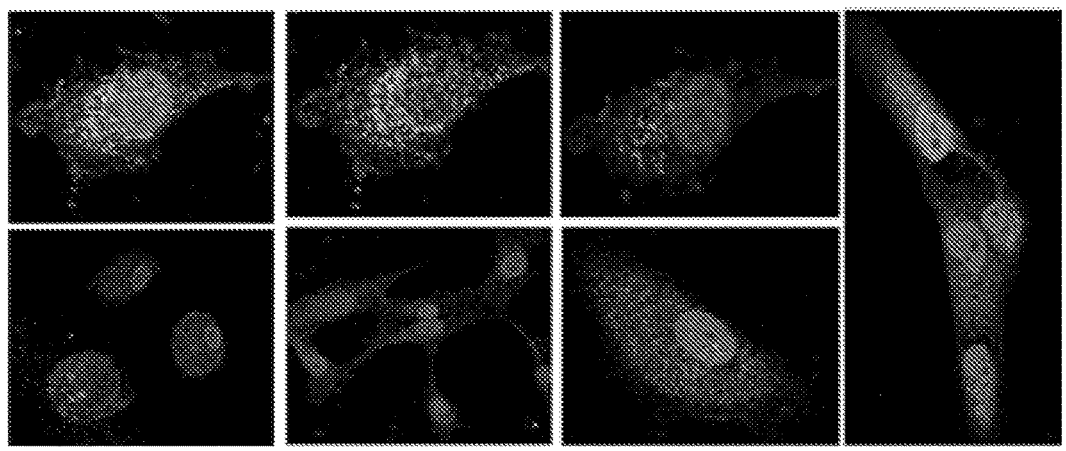
FIG. 27 are confocal images of CTCs cultured for seven days.

Once the cells are fixed, the cells are stained for: (1) DAPI, a nuclear stain shown in blue, (2) CK19, an epithelial marker observed as a cytoplasmic stain shown in FITC channel (green); and (3) a nuclear marker shown in PE channel (red). The last one is a nuclear marker that its expression is promoted on cancer cells that are co-cultured with CAFs. Since the conditioning media is obtained from CAFs, it is expected to see this expression on CTCs. Also, CK19 serves as a positive marker for CTCs since CAFs are not able to express cytokeratin. FIG. 27 shows staining results for identified CTCs, where expression of the three cell markers is seen, which is expected.

Genomic Assays of CTCs:

CTCs are highly heterogeneous, and their molecular characterization can not only to confirm their malignant origin but can also help to discover what immunophenotypic changes occur as the tumor progresses. This will allow the identification of diagnostically and therapeutically relevant targets to stratify cancer patients for individualized therapies. The labyrinth channel structure accomplishes the isolation and purification of CTCs, facilitating protein expression analysis at a cell transcript level. Therefore, the RNA is successfully extracted from all sixteen samples processed with the labyrinth.

It is believed that performing gene expression analysis of the pancreatic patient samples gives a more comprehensive perceptive of CTCs for each individual patient. Heterogeneity results obtained in the gene expression level also gives a better insight on the diverse pool of CTC subpopulations observed using the immunocytochemistry approach. Genomic assays may facilitate a better understanding of the variable tumor initiating capability within the same CTC population.

One or more of the values described above may vary by ±5%, ±10%, ±15%, ±20%, ±25%, etc. so long as the variance remains within the scope of the disclosure. Unexpected results may be obtained from each member of a Markush group independent from all other members. Each member may be relied upon individually and or in combination and provides adequate support for specific embodiments within the scope of the appended claims. The subject matter of all combinations of independent and dependent claims, both singly and multiply dependent, is herein expressly contemplated. The disclosure is illustrative including words of description rather than of limitation. Many modifications and variations of the present disclosure are possible in light of the above teachings, and the disclosure may be practiced otherwise than as specifically described herein.

What is claimed is:

1. A microfluidic device for detecting rare cells in a fluid sample comprising the rare cells and other cells, the microfluidic device comprising:
   an inlet for receiving the fluid sample;
   a labyrinth channel structure in fluid communication with the inlet and comprising at least one channel through which the fluid sample flows with the at least one channel having a rectangular cross-section, a width of from 500 to 1000 µm, and a height of from 1 to 150 µm, the at least one channel having a plurality of segments and a plurality of corners with each corner defined between adjacent segments to induce separation of the rare cells from the other cells in the fluid sample as the rare cells move to a first equilibrium position within the at least one channel when a ratio of inertial lift forces ($F_z$) and Dean flow ($F_D$) of the fluid sample is from 2 to 10; and
   an outlet in fluid communication with the at least one channel for collecting the rare cells separated from the other cells in the fluid sample.

2. The microfluidic device as set forth in claim 1 wherein the labyrinth channel structure comprises at least 2 corners.

3. The microfluidic device as set forth in claim 1 wherein the labyrinth channel structure comprises from 40 to 50 corners.

4. The microfluidic device as set forth in claim 1 wherein the other cells include white blood cells, and the at least one channel has the plurality of segments and the plurality of corners to induce separation of the white blood cells as the white blood cells move to a second equilibrium position within the at least one channel wherein a ratio of inertial lift forces ($F_z$) and Dean flow ($F_D$) of the fluid sample is from 1 to 5.

5. The microfluidic device as set forth in claim 4 wherein the first equilibrium position defines a first stream comprising rare cells and the second equilibrium position defines a second stream comprising white blood cells, and wherein a spacing between the first and second stream is from 50 to 100 µm.

6. The microfluidic device as set forth in claim 1 wherein the at least one channel has a length of from 1 µm to 1000 µm.

7. The microfluidic device as set forth in claim 1 wherein the labyrinth channel structure is configured to separate at least rare cells and white blood cells, and the outlet comprises a first flow path for the rare cells and a second flow path for the white blood cells.

8. The microfluidic device as set forth in claim 1 wherein each of the plurality of corners induces at least a 90° change in direction of the flow of the fluid sample.

9. A method of detecting rare cells in a fluid sample comprising the rare cells and other cells, the method comprising the steps of:
   providing a microfluidic device comprising:
      an inlet;
      a labyrinth channel structure in fluid communication with the inlet and comprising at least one channel having a plurality of segments and a plurality of corners with each corner defined between adjacent segments with the at least one channel having a rectangular cross-section, a width of from 500 to 1000 μm, and a height of from 1 to 150 μm; and an outlet in fluid communication with the at least one channel;

introducing the fluid sample into the inlet of the microfluidic device;

flowing the fluid sample through the labyrinth channel structure of the microfluidic device; and separating the rare cells from the other cells as the fluid sample flows past the plurality of corners in the at least one channel of the labyrinth channel structure, the rare cells moving to a first equilibrium position within the at least one channel when a ratio of inertial lift forces ($F_z$) and Dean flow ($F_D$) of the fluid sample is from 2 to 10.

10. The method as set forth in claim 9 wherein the step of separating of the rare cells is further defined as separating the rare cells from the other cells as the fluid sample flows through 40 to 50 corners.

11. The method as set forth in claim 9 wherein the step of introducing of the fluid sample into the inlet is further defined as introducing the fluid sample at a volumetric flow rate of from 0.1 to 30 mL/hr.

12. The method as set forth in claim 9 wherein the other cells comprise white blood cells and the method further comprises the step of separating the white blood cells as the fluid sample flows past the plurality of corners in the at least one channel of the labyrinth channel structure, the white blood cells moving to a second equilibrium position within the at least one channel when a ratio of inertial lift forces ($F_z$) and Dean flow ($F_D$) of the fluid sample is from 1 to 5.

13. The microfluidic device as set forth in claim 12 wherein the separating of the rare cells is further defined as separating the rare cells into a first stream and the separating of the white blood cells is further defined as separating the white blood cells into a second stream, and wherein separation between the first and second stream is from 50 to 100 μm.

14. The method as set forth in claim 9 wherein the other cells comprise white blood cells and the outlet comprises a first flow path for the rare cells and a second flow path for the white blood cells, and wherein the method further comprises the step of collecting the rare cells in the first flow path and collecting the white blood cells in the second flow path.

15. The method as set forth in claim 9 further comprising the step of recovering at least 95% of the rare cells after the method step of separating the rare cells from the other cells.

16. A microfluidic device for detecting rare cells in a fluid sample comprising the rare cells and other cells, the microfluidic device comprising:

an inlet for receiving the fluid sample;

at least one channel having a plurality of segments and a plurality of corners to separate the rare cells from the other cells in the fluid sample by causing the rare cells to move to an equilibrium position within a flow of the fluid sample when a ratio of inertial lift forces ($F_z$) and Dean flow ($F_D$) of the fluid sample is from 2 to 10, wherein each of the plurality of channels having a rectangular cross-section, a width of from 500 to 1000 μm, and a height of from 1 to 150 μm; and an outlet for collecting the rare cells.

17. The microfluidic device as set forth in claim 16 wherein the other cells include white blood cells, and presence of the plurality of corners in the at least one channel induces separation of the white blood cells as the white blood cells move to a second equilibrium position within the at least one channel wherein a ratio of inertial lift forces ($F_z$) and Dean flow ($F_D$) of the fluid sample is from 1 to 5.

18. The microfluidic device as set forth in claim 17 wherein the equilibrium position defines a first stream comprising rare cells and the second equilibrium position defines a second stream comprising white blood cells, and wherein a spacing between the first and second stream is from 50 to 100 μm.

19. The microfluidic device as set forth in claim 16 wherein the at least one channel has a length of from 1 μm to 1000 μm.

20. The microfluidic device as set forth in claim 16 wherein the at least one channel is configured to separate at least rare cells and white blood cells, and the outlet comprises a first flow path for the rare cells and a second flow path for the white blood cells.

* * * * *